(12) United States Patent
Ukrainsky et al.

(10) Patent No.: US 11,826,024 B2
(45) Date of Patent: Nov. 28, 2023

(54) MULTI-ORGAN IMAGING SYSTEM WITH A SINGLE, MULTI-EXAMINATION ILLUMINATION UNIT

(71) Applicants: Gennady Ukrainsky, New York, NY (US); Rada Sumareva, New York, NY (US); Daniel Kogan, Brooklyn, NY (US); Sergei Kuznetsov, Voorhees, NY (US)

(72) Inventors: Gennady Ukrainsky, New York, NY (US); Rada Sumareva, New York, NY (US); Daniel Kogan, Brooklyn, NY (US); Sergei Kuznetsov, Voorhees, NY (US)

(73) Assignee: ZIPHYCARE INC, New York, NY (US)

( * ) Notice: Subject to any disclaimer, the term of this patent is extended or adjusted under 35 U.S.C. 154(b) by 0 days.

(21) Appl. No.: 17/541,253

(22) Filed: Dec. 3, 2021

(65) Prior Publication Data
US 2022/0175231 A1    Jun. 9, 2022

Related U.S. Application Data

(60) Provisional application No. 63/120,800, filed on Dec. 3, 2020.

(51) Int. Cl.
*A61B 1/05* (2006.01)
*A61B 1/227* (2006.01)
(Continued)

(52) U.S. Cl.
CPC .......... *A61B 1/05* (2013.01); *A61B 1/00043* (2013.01); *A61B 1/00188* (2013.01);
(Continued)

(58) Field of Classification Search
CPC .......... A61B 1/00018; A61B 1/00052; A61B 1/00055; A61B 1/00066; A61B 1/00087;
(Continued)

(56) References Cited

U.S. PATENT DOCUMENTS 6,221,007 B1 * 4/2001 Green ................ A61B 1/00052
600/106
6,251,070 B1   6/2001 Khazaka
(Continued)

FOREIGN PATENT DOCUMENTS

CN            204879378 U     12/2015

*Primary Examiner* — Aaron B Fairchild
*Assistant Examiner* — Stephen Floyd London
(74) *Attorney, Agent, or Firm* — Ashok Tankha

(57) ABSTRACT

A multi-organ imaging system including a camera lens, a stationary, multi-examination illumination unit (SMEIU), and an attachment holder is provided. An industrial camera unit (ICU) for imaging multiple organs, for example, ear, nose, throat, and skin, is housed in a camera body. The camera lens has a fixed focal length and an iris for optimizing examination and imaging of the organs. The SMEIU is integrated to the camera body and includes illuminators arranged in a geometrical configuration. The attachment holder accommodates an organ examination attachment selected for examining an organ. The illuminators, in optical communication with one or more reflective surfaces in the organ examination attachment, produce shadowless illumination during examination and imaging of each organ, without requiring replacement of the SMEIU for examining each organ. A display unit, accommodated in a display holder detachably attached to the camera body, assists in aiming the camera lens and visualizing each organ.

17 Claims, 15 Drawing Sheets

(51) Int. Cl.
  *A61B 1/233* (2006.01)
  *A61B 1/06* (2006.01)
  *A61B 1/00* (2006.01)
  *A61B 1/267* (2006.01)
  *A61B 1/045* (2006.01)

(52) U.S. Cl.
  CPC ............ *A61B 1/045* (2013.01); *A61B 1/0684* (2013.01); *A61B 1/227* (2013.01); *A61B 1/233* (2013.01); *A61B 1/267* (2013.01)

(58) Field of Classification Search
  CPC ............ A61B 1/00096; A61B 1/00101; A61B 1/00105; A61B 1/00121; A61B 1/00124; A61B 1/00126; A61B 1/00128; A61B 1/00135; A61B 1/00137; A61B 1/0014; A61B 1/00142; A61B 1/042; A61B 1/0646; A61B 1/0669; A61B 1/0684; A61B 1/247; A61B 1/32; F16M 11/041; F16M 11/14
  See application file for complete search history.

(56) References Cited

U.S. PATENT DOCUMENTS

| | | |
|---|---|---|
| 7,714,897 B2 | 5/2010 | Makela et al. |
| 8,643,701 B2 | 2/2014 | Nguyen |
| 2003/0050534 A1* | 3/2003 | Kazakevich ......... A61B 1/0607 600/179 |
| 2005/0200707 A1* | 9/2005 | Yogesan ............ A61B 1/00105 348/207.99 |
| 2008/0158349 A1* | 7/2008 | Miller ................ A61B 1/00087 348/82 |
| 2010/0171827 A1* | 7/2010 | Wu ........................ A61B 3/185 348/135 |
| 2010/0214435 A1* | 8/2010 | Chang .................... H04N 23/88 348/E9.051 |
| 2012/0289858 A1* | 11/2012 | Ouyang ................. A61B 1/045 600/562 |
| 2013/0128223 A1* | 5/2013 | Wood ................... A61B 3/1208 351/246 |
| 2013/0155249 A1 | 6/2013 | Neeley |
| 2015/0305603 A1* | 10/2015 | Gal ...................... A61B 1/0669 600/109 |
| 2016/0338590 A1* | 11/2016 | Sagalovich .............. A61B 1/07 |
| 2017/0258299 A1* | 9/2017 | Aikawa ............. A61B 1/00089 |
| 2017/0273539 A1* | 9/2017 | Law .................... A61B 1/00126 |
| 2017/0318205 A1* | 11/2017 | Duckett, III ............. A61B 1/07 |
| 2019/0133432 A1* | 5/2019 | Tsai .................... A61B 1/0684 |
| 2019/0150723 A1* | 5/2019 | Iwama .................. A61B 1/042 |
| 2019/0208988 A1* | 7/2019 | Takatsuji ............. A61B 1/0052 |
| 2019/0357758 A1* | 11/2019 | Malinskiy ............ A61B 1/0638 |
| 2019/0357760 A1* | 11/2019 | Nara ........................ A61B 1/05 |
| 2021/0219816 A1* | 7/2021 | Truckai .................. A61B 5/067 |
| 2022/0031145 A1* | 2/2022 | Takahashi .......... A61B 1/00177 |

* cited by examiner

MULTI-ORGAN IMAGING SYSTEM WITH A SINGLE, MULTI-EXAMINATION ILLUMINATION UNIT

CROSS-REFERENCE TO RELATED APPLICATIONS

This application claims priority to and the benefit of the provisional patent application titled "Industrial Camera Unit (ICU) For Performing Ear, Nose, Throat (ENT) And Skin Imaging", application No. 63/120,800, filed in the United States Patent and Trademark Office on Dec. 3, 2020. The specification of the above referenced patent application is incorporated herein by reference in its entirety.

BACKGROUND

Micro-sized or miniaturized cameras are typically used during investigative medical procedures such as ear, nose, and throat (ENT) examination procedures including an otoscopy, a rhinoscopy, a laryngoscopy, etc., to capture images of a target area within a body cavity such as an aural cavity, a nasal cavity, an oral cavity, etc., of a patient. A camera typically includes a light source or an illuminator for illuminating the target area and a lens for capturing images of the target area. Conventional camera systems have several deficiencies, for example, large size, need for manual focusing, poor resolution, inadequate lighting, color reproduction issues, white balance issues, clarity and brightness issues, shadows and bright spots produced during illumination, etc.

In a typical medical examination procedure, for example, an otoscopy, a rhinoscopy, or a laryngoscopy, a camera lens is mounted in front of a particular scope device used for the medical examination procedure, and connected to an external display screen at a location away from a location of examination. In this case, a health care worker, for example, a doctor, may find it difficult to coordinate his or her hands and eyes smoothly as the doctor pays more attention to the display screen positioned away from the location of examination and less attention to the scope device and/or medical examination instruments that are inserted inside a patient's body cavity, which may cause movements of the scope device and/or the medical examination instruments in the patient's body cavity, resulting in discomfort to the patient.

Furthermore, conventional scope devices used for different medical examination procedures are tailored for a particular use. For example, a laryngoscope is configured for a particular use in procedures involving a larynx, such as a laryngoscopy. Similarly, many other scope devices such as a keratoscope, an opthalmoscope, an otoscope, a rhinoscope, etc., are typically configured for a specific purpose. For example, the keratoscope is configured for examining the cornea of an eye to detect irregularities in its anterior surface; the opthalmoscope is configured for examining the retina and other interior structures of the eye; the otoscope is configured for examining the eardrum and other interior structures of the ear; and the rhino scope is configured for examining nasal passages through the nasopharynx. The otoscope is also configured for examining surrounding tissues of a throat area. Because these scope devices are typically configured for a particular use, they are not readily interchangeable with each other. Therefore, in order to be able to perform more than one medical examination procedure, a health care worker needs to have access to different scope devices which may create several issues for the health care worker. For example, the different scope devices and their respective camera systems take up more space, when stored, than does a single instrument, making them more difficult to carry into the field and in turn, less portable. Moreover, the health care worker has to put in substantial effort to keep changing the scope device and their respective camera systems for each type of examination.

Some ear, nose, and throat (ENT) examination procedures use medical imaging systems comprising industrial camera units and different attachments for performing ear, nose, throat, and skin imaging. Each of these attachments requires a specific light source or illuminator for illuminating a target area of the ear, the nose, the throat, or the skin, which requires the illuminator to be replaced or exchanged during examination of each of these organs. The requirement for illuminators to be replaced or exchanged during examination of each different organ increases the cost of these medical imaging systems and decreases the flexibility of using these medical imaging systems. Moreover, a health care worker who performs the examination requires a certain amount of skill to replace the illuminator for each type of examination. Furthermore, the illuminators used in conventional medical imaging systems typically produce shadows and bright spots during examination and imaging of the organs, which may cause misinterpretation of the captured images and improper diagnosis.

Hence, there is a long-felt need for a multi-organ imaging system with a single, integrated, multi-examination illumination unit that does not need to be replaced during examination of different organs, for example, ear, nose, throat, skin, eyes, etc. Moreover, there is a need for a multi-organ imaging system that allows different scope devices to be readily interchanged on a single camera body of the multi-organ imaging system for conveniently performing different medical examination procedures. Furthermore, there is a need for a multi-organ imaging system with an illumination unit that produces shadowless illumination without bright spots during examination and imaging of different organs. Furthermore, there is a need for a multi-organ imaging system with an optimized camera lens that provides a broad field of view in a body cavity, and an industrial camera unit enhanced in pixel resolution and color depth. Furthermore, there is a need for a portable multi-organ imaging system with a detachable display unit that allows optimal hand-eye coordination, camera aiming, and media transmission during examination and imaging of different organs.

SUMMARY

This summary is provided to introduce a selection of concepts in a simplified form that are further disclosed in the detailed description. This summary is not intended to determine the scope of the claimed subject matter.

The system disclosed herein addresses the above-recited need for a multi-organ imaging system with a single, integrated, multi-examination illumination unit that does not need to be replaced during examination of different organs, for example, ear, nose, throat, skin, eyes, etc. The multi-organ imaging system allows different scope devices, for example, a throat and skin examination attachment, an otoscope attachment, etc., to be readily interchanged on a single camera body of the multi-organ imaging system for conveniently performing different medical examination procedures. The multi-organ imaging system with the single, integrated, multi-examination illumination unit produces shadowless illumination without bright spots during examination and imaging of different organs. The multi-organ imaging system comprises an optimized camera lens that provides a broad field of view in a body cavity, and an industrial camera unit enhanced in pixel resolution and color depth. The multi-organ imaging system disclosed herein is configured for performing ear, nose, and throat (ENT) imaging, skin imaging, retinal imaging, etc., without requiring replacement or exchange of the single, integrated, multi-examination illumination unit when one type of examination is changed to another type of examination. The multi-organ imaging system with the single, integrated, multi-examination illumination unit allows health care workers with limited skills to perform ENT imaging, skin imaging, retinal imaging, etc. Furthermore, the system disclosed herein addresses the above-recited need for a portable multi-organ imaging system with a detachable display unit that allows optimal hand-eye coordination, camera aiming, and media transmission during examination and imaging of different organs.

The multi-organ imaging system disclosed herein comprises a camera body, a camera lens, a stationary, multi-examination illumination unit, an attachment holder, a display mounting member, and control elements. The camera body comprises a first end, a second end, and a cavity defined between the first end and the second end. The camera body is configured to house an industrial camera unit within the cavity. The industrial camera unit is configured for imaging multiple organs, for example, ear, nose, throat, skin, eyes, etc. The industrial camera unit is enhanced with pixel resolution and color depth. The camera lens is operably coupled to the industrial camera unit. The camera lens has a fixed focal length and an iris for optimizing examination and the imaging of the organs using the industrial camera unit. The camera lens is selected to provide a broad field of view in a body cavity of a patient. For example, the camera lens is selected to provide a sharp view of an entirety of a mouth of a patient when the camera body is positioned at a predefined distance from the throat of the patient. In an embodiment, the multi-organ imaging system further comprises gripping elements attached to an outer surface of the camera body. The gripping elements are configured to provide a soft, non-slip grip of the camera body to an operator of the multi-organ imaging system.

The stationary, multi-examination illumination unit is integrated to the camera body, proximal to the camera lens. The stationary, multi-examination illumination unit comprises multiple illuminators arranged in a geometrical configuration, for example, a circular configuration, thereon. In an embodiment, the illuminators of the stationary, multi-examination illumination unit are selected from surface mount technology (SMT) light emitting diodes (LEDs) and through-hole LEDs. The attachment holder is attached to the first end of the camera body, in coaxial communication with the stationary, multi-examination illumination unit positioned in front of the attachment holder. The attachment holder is configured to coaxially accommodate an organ examination attachment selected for examining one or more of the organs. The organ examination attachment is selected, for example, from a throat and skin examination attachment and an otoscope attachment. In an embodiment, the attachment holder is a ring-shaped element configured to coaxially accommodate the organ examination attachment thereon. The illuminators of the stationary, multi-examination illumination unit, in optical communication with one or more reflective surfaces configured in the organ examination attachment, are configured to produce shadowless illumination without bright spots during the examination and the imaging of each of the organs, without requiring replacement of the stationary, multi-examination illumination unit for the examination and the imaging of each of the organs.

In an embodiment, the multi-organ imaging system further comprises a reflective layer positioned in the organ examination attachment for assisting the stationary, multi-examination illumination unit in producing the shadowless illumination during the examination and the imaging of each of the organs.

In an embodiment, the multi-organ imaging system further comprises a protective filter coaxially positioned on a front end of the throat and skin examination attachment over the camera lens and the stationary, multi-examination illumination unit. The protective filter is configured to protect the camera lens and the illuminators of the stationary, multi-examination illumination unit. The illuminators are positioned away from an optical axis passing through the camera body, at a distance from an outer edge of the protective filter. In an embodiment, the multi-organ imaging system further comprises a light diffuser coupled to an inner periphery of the protective filter. The light diffuser is configured to scatter light received from the illuminators of the stationary, multi-examination illumination unit for producing shadowless light for illuminating a target area. In an embodiment, the multi-organ imaging system further comprises a light guard positioned proximal to the camera lens and the stationary, multi-examination illumination unit. The light guard is configured to prevent reflection of light from the stationary, multi-examination illumination unit and the protective filter into the camera lens. In an exemplary implementation, the stationary, multi-examination illumination unit is a stationary integrated illumination unit that provides shadowless illumination without bright spots; has brightness control; is integrated with the camera body and shares the protective filter with the camera lens; has a light guard to prevent light reflection from the stationary, multi-examination illumination unit and the protective filter into the camera lens; and has specialized reflective surfaces to provide enhanced shadowless illumination in combination with the illuminators. The illuminators, for example, through-hole or surface mount technology (SMT) light emitting diodes (LEDs), are placed a short distance away from the optical axis than the edge of the protective filter.

In an embodiment, the organ examination attachment is an otoscope attachment comprising an otoscope support member, a focusing cone, a supplemental lens, a speculum, and a light separator. The otoscope support member is coaxially accommodated on the attachment holder. The otoscope support member comprises a reflective inner surface. The focusing cone is attached to a front end of the otoscope support member. The focusing cone comprises a lens holder configured to accommodate the supplemental lens. The supplemental lens, in optical communication with the camera lens in the camera body, is configured to change a focusing distance of the industrial camera unit to cover a predetermined depth of an ear channel. The speculum is operably coupled to a front end of the focusing cone for examining the ear channel and allowing imaging of the ear channel by the industrial camera unit via the camera lens. The light separator comprises a reflective outer surface configured to form a light tunnel in optical communication with the reflective inner surface of the otoscope support member and the stationary, multi-examination illumination unit for assisting in the production of the shadowless illumination during the examination of the ear channel.

In an embodiment, the display mounting member of the multi-organ imaging system is operably coupled to and extends outwardly from the second end of the camera body. In an embodiment, the display mounting member is configured in a spherical shape for allowing movement of a display unit, for example, a tablet computing device, accommodated in a display holder, in multiple dimensions, for example, three dimensions. The display mounting member of the spherical shape is herein referred to as a spherical mount. The display mounting member is configured to detachably attach to a clamping member, for example, a chuck, of the display holder. The clamping member is attached to a rear surface of the display holder. The clamping member is configured to detachably engage with the display mounting member, for example, the spherical mount, positioned at the second end of the camera body for detachably attaching the display unit to the camera body.

The display holder securely accommodates the display unit, for example, a tablet computing device, that assists in aiming the camera lens and visualizing one or more of the organs. The display unit is configured to receive a media stream of each of the visualized organs captured by the industrial camera unit via the camera lens. In an embodiment, the display unit receives the media stream of each of the visualized organs from an external computing device, for example, via a wired connection and/or a wireless connection. In another embodiment, the display unit receives the media stream of each of the visualized organs directly from the industrial camera unit. The industrial camera unit, in optical communication with the camera lens, is configured to capture and display images of a target area of one of the organs. The industrial camera unit is configured to store multiple imaging parameters that are invoked at activation or power up of the multi-organ imaging system. The imaging parameters comprise, for example, a predefined standard red, green, and blue (RGB) gamma value, front light illumination, front light compensation, daylight color balance, auto white balance, fixed white balance, auto exposure activation, optional image sharpening, etc. In an embodiment, the multi-organ imaging system further comprises a connector positioned on the second end of the camera body. The connector is configured to connect a media and power cable, for example, a video and power cable, to the industrial camera unit in the camera body and transmit a media stream of each of the organs captured by the industrial camera unit via the camera lens, to an external computing device, and to receive commands from the external computing device. In an embodiment, the industrial camera unit transmits the captured media stream of each of the organs directly to the display unit accommodated in the display holder.

In an embodiment, the multi-organ imaging system further comprises a tool mounting member attached to the first end of the camera body. The tool mounting member is configured to mount and detachably attach a medical tool, for example, a tongue depressor, a skin attachment, etc., that allows an unobstructed view of one of the organs, for example, the throat, the skin, etc., during the examination and the imaging of the organ. In an embodiment, the multi-organ imaging system further comprises a control element, for example, a snap button, positioned on either the camera body, or the display unit, or a remote device operably connected to the multi-organ imaging system via a network. Activation of the control element triggers a capture a snapshot of a target area of one of the organs by the industrial camera unit via the camera lens. In an embodiment, the multi-organ imaging system communicates the activation of the control element to an operator of the multi-organ imaging system via an audio signal. In an embodiment, one or more control elements are positioned on the outer surface of the camera body. These control elements are configured to adjust illumination settings, for example, brightness, of the stationary, multi-examination illumination unit.

In one or more embodiments, related systems comprise image processing, storage, and transmission circuitry and/or programming for executing the methods disclosed herein. The image processing, storage, and transmission circuitry and/or programming are of any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The foregoing summary, as well as the following detailed description, is better understood when read in conjunction with the appended drawings. For illustrating the embodiments herein, exemplary constructions of the embodiments are shown in the drawings. However, the embodiments herein are not limited to the specific structures and components disclosed herein. The description of a structure or a component referenced by a numeral in a drawing is applicable to the description of that structure or component shown by that same numeral in any subsequent drawing herein.

DETAILED DESCRIPTION

Figure 1:
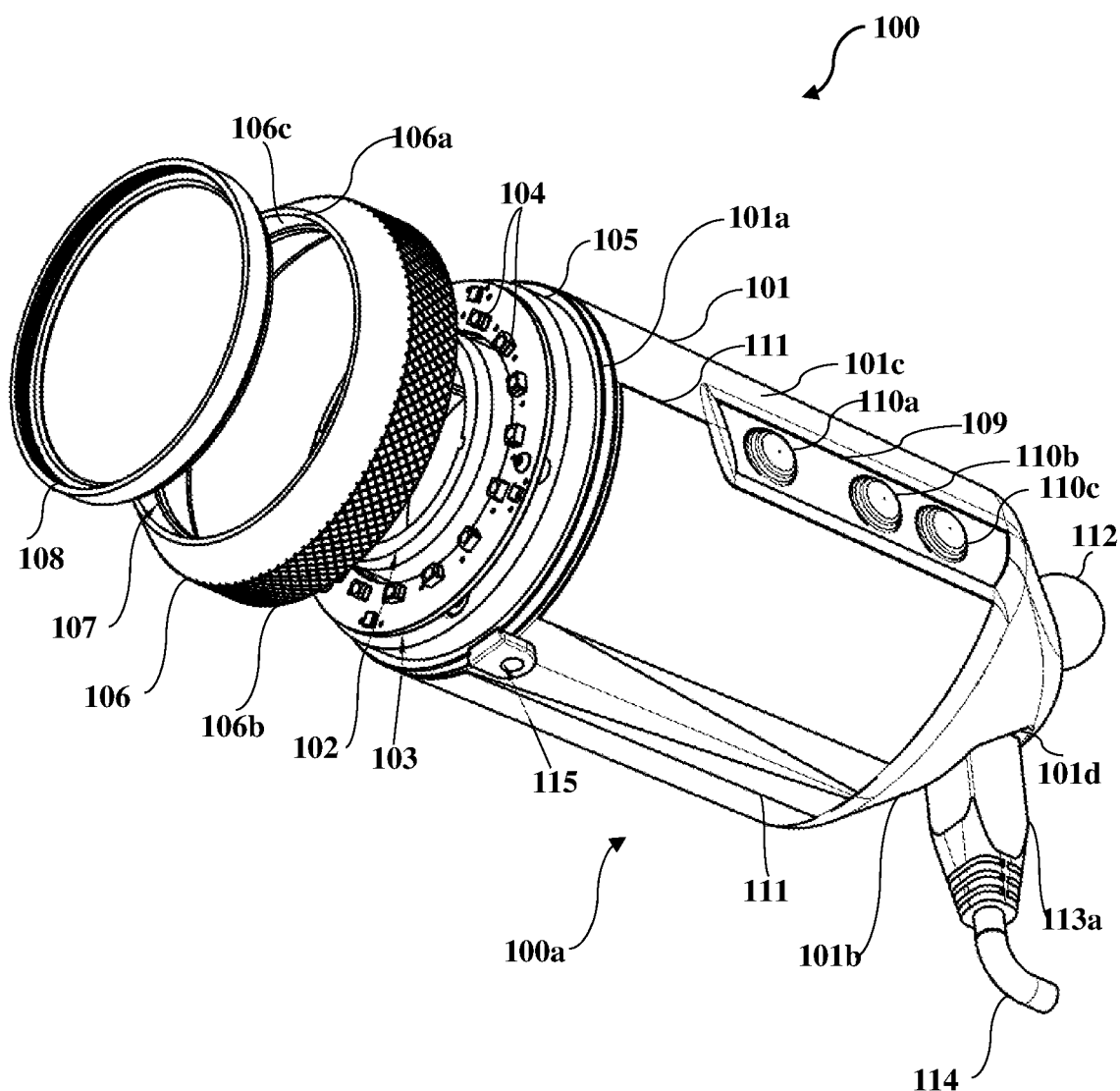
FIG. 1 exemplarily illustrates a partially exploded, bottom perspective view of an embodiment of a multi-organ imaging system with a single, integrated, multi-examination illumination unit for performing throat and skin examination and imaging.

FIG. 1 exemplarily illustrates a partially exploded, bottom perspective view of an embodiment of a multi-organ imaging system 100 with a single, integrated, multi-examination illumination unit 103 for performing throat and skin examination and imaging. The single, integrated, multi-examination illumination unit 103 is a stationary illumination unit configured for examining multiple different organs, for example, ear, nose, throat, skin, eyes, etc., without requiring to be replaced or exchanged for each type of examination. The multi-organ imaging system 100 allows different scope devices, for example, a throat and skin examination attachment 106 exemplarily illustrated in FIG. 1 and FIGS. 4B-4C, FIGS. 5A-5C, an otoscope attachment 132 exemplarily illustrated in FIGS. 7-9B, etc., to be readily interchanged on a single camera body 101 of the multi-organ imaging system 100 for conveniently performing different medical examination procedures, for example, a laryngoscopy, a skin examination, an otoscopy, an eye examination such as a retinal examination, etc. The camera body 101 with each scope device or organ examination attachment, for example, 106, 132, etc., provides an enclosed surface free of openings for easy cleaning and disinfection between patient visits. The enclosed camera body 101 precludes germs for entering the camera body 101.

The multi-organ imaging system 100 with the single, integrated, multi-examination illumination unit 103 produces shadowless illumination without bright spots during examining and imaging of different organs. The multi-organ imaging system 100 comprises an optimized camera lens 102 that provides a broad field of view in a body cavity, and an industrial camera unit 118 enhanced in pixel resolution and color depth. The multi-organ imaging system 100 disclosed herein is configured for performing ear, nose, and throat (ENT) imaging, skin imaging, retinal imaging, etc., without requiring replacement or exchange of the single, integrated, multi-examination illumination unit 103 when changing from one type of examination to another type of examination. The multi-organ imaging system 100 with the single, integrated, multi-examination illumination unit 103 allows operators, for example, health care workers with limited skills to perform ENT imaging, skin imaging, retinal imaging, etc. The multi-organ imaging system 100 is a portable imaging system with a detachable display unit 125, for example, a tablet computing device, that allows optimal hand-eye coordination, camera aiming, and media transmission during examination and imaging of different organs.

As exemplarily illustrated in FIG. 1, the multi-organ imaging system 100 disclosed herein comprises a camera body 101, a camera lens 102, a stationary, multi-examination illumination unit 103, and an attachment holder 105. The camera body 101 comprises a first end 101a and a second end 101b. The camera body 101 further comprises a cavity 101e exemplarily illustrated in FIG. 2, defined between the first end 101a and the second end 101b. The camera body 101 is made of a material having high stiffness, for example, any one of stainless steel, plastic, composite materials, polycarbonate compounds containing a predetermined percentage of glass fiber, diecast metal such as diecast aluminum, magnesium, diecast metal alloys, silicon, etc. In an embodiment, the camera body 101 is enclosed and sealed for convenient cleaning of the camera body 101. In an embodiment, the multi-organ imaging system 100 further comprises gripping elements 111 attached to an outer surface 101c of the camera body 101. The gripping elements 111 are configured to provide a soft, non-slip grip of the camera body 101 to an operator of the multi-organ imaging system 100. The gripping elements 111 are made of, for example, soft, non-slip rubber or silicone materials. The camera body 101 is configured to house an industrial camera unit 118 as exemplarily illustrated in FIG. 2, within the cavity 101e. The industrial camera unit 118 is configured for imaging multiple different organs, for example, ear, nose, throat, skin, eyes, etc.

The camera lens 102 is operably coupled to the industrial camera unit 118. The camera lens 102 is mounted onto the industrial camera unit 118, for example, using a C-mount. The camera lens 102 comprises an optical lens or an assembly of lenses used in operable communication with the industrial camera unit 118 in the camera body 101 to capture images of a target area of an organ, for example, the throat, the skin, the nose, or the ear. As used herein, the term "images" refers to digital still images and/or digital video frames. The camera lens 102 is made, for example, from glass, quartz glass, fluorite, or plastics such as acrylic, or groups of glass elements. The camera lens 102 has a fixed focal length, an iris (not shown), and a focus mechanism (not shown) for optimizing examination and the imaging of the organs using the industrial camera unit 118. The focal length of the camera lens 102 is, for example, about 10 millimeters (mm). The iris is configured, for example, to an f-stop or an f-number of f/8, to control the depth of the field of view of the camera lens 102. The depth of the field of view provided by the camera lens 102 is, for example, about 50 mm inside a patient's mouth. In an embodiment, the iris comprises a number of thin plates or blades that are arranged to create a circular opening or an aperture in the center.

Light, after passing through the iris opening, strikes on an image sensor in the industrial camera unit 118, which converts the light into electrical pulses, thereby creating an image or a video. The fixed focal length and the fixed iris of the camera lens 102 simplify examination operations, requiring an operator of the multi-organ imaging system 100 to bring the multi-organ imaging system 100 up to a predefined distance, for example, about 100 mm to about 120 mm, to a target area of a patient's organ and aim at the target area. The focus mechanism is set during production tuning of the camera lens 102. In an embodiment, the camera lens 102 comprises a set iris configured to provide a predetermined depth of sharpness for a medical examination procedure, for example, a laryngoscopy. For an examination of the throat, the camera lens 102 is selected to provide a sharp view of an entirety of a patient's mouth when the camera body 101 is positioned at a predefined distance from the patient's throat. For example, the camera lens 102 is selected to provide a sharp whole mouth view when the multi-organ imaging system 100 is, for example, 120 mm from the throat, and to cover a 100 mm width with 60 mm depth in the patient's mouth.

The stationary, multi-examination illumination unit 103 is integrated and affixed to the camera body 101, proximal to the camera lens 102 and in front of the attachment holder 105. The stationary, multi-examination illumination unit 103 comprises multiple illuminators 104 arranged in a geometrical configuration, for example, a circular configuration, thereon. In an embodiment, the illuminators 104 of the stationary, multi-examination illumination unit 103 are selected from surface mount technology (SMT) light emitting diodes (LEDs) and through-hole LEDs. The stationary, multi-examination illumination unit 103 is configured as a printed circuit board (PCB) assembly onto which the illuminators 104 are mounted and operably coupled. In an embodiment, the illuminators 104 are soldered on a flame retardant (FR)-4 glass-reinforced epoxy resin laminate to form the stationary, multi-examination illumination unit 103. In another embodiment, the illuminators 104 are soldered on a metal core PCB, for example, an aluminum core PCB, to form the stationary, multi-examination illumination unit 103. The aluminum core PCB comprises a thin layer of thermally conductive dielectric material configured to transfer and dissipate heat with optimal efficiency.

The attachment holder 105 is attached to the first end 101*a* of the camera body 101, in coaxial communication with the stationary, multi-examination illumination unit 103 positioned in front of the attachment holder 105. The attachment holder 105 is configured to coaxially accommodate an organ examination attachment selected for examining one or more of the organs. In an embodiment, the attachment holder 105 is a ring-shaped element or mount configured to coaxially accommodate the organ examination attachment thereon. The organ examination attachment is selected, for example, from a throat and skin examination attachment 106 exemplarily illustrated in FIG. 1, FIGS. 4B-4C, and FIGS. 5A-5C, and an otoscope attachment 132 exemplarily illustrated in FIGS. 7-9B. For purposes of illustration, the detailed description refers to the organ examination attachment being a throat and skin examination attachment 106 as exemplarily illustrated in FIG. 1, FIGS. 4B-4C, and FIGS. 5A-5C, or an otoscope attachment 132 as exemplarily illustrated in FIGS. 7-9B; however, the scope of the multi-organ imaging system 100 is not limited to the organ examination attachment being a throat and skin examination attachment 106 or an otoscope attachment 132, but may be extended to include other scope devices, for example, a rhinoscope, a keratoscope, an opthalmoscope, etc., used in ear, nose, and throat (ENT) and other examination procedures. In an embodiment, the organ examination attachment is configured to fit together with the attachment holder 105, for example, by screw threads. In another embodiment, the organ examination attachment is configured to fit together with the attachment holder 105, for example, by an annular snap-fit, or press-fit, or friction-fit attachment method.

FIG. 1 shows a throat and skin examination attachment 106 configured for coaxially accommodation on the attachment holder 105. The throat and skin examination attachment 106 comprises a front end 106*a* and a rear end 106*b*. In an embodiment as exemplarily illustrated in FIG. 1, the attachment holder 105 is a ring-shaped element or mount configured to coaxially accommodate the throat and skin examination attachment 106 thereon, such that the rear end 106*b* of the throat and skin examination attachment 106 sits firmly on the attachment holder 105. In an embodiment, the multi-organ imaging system 100 further comprises a reflective layer 107 positioned in the throat and skin examination attachment 106 for assisting the stationary, multi-examination illumination unit 103 in producing shadowless illumination during the examination and the imaging of each of the organs, for example, the throat, the skin, etc. The reflective layer 107 is positioned on an inner periphery 106*c* of the throat and skin examination attachment 106. The illuminators 104 of the stationary, multi-examination illumination unit 103, in optical communication with one or more reflective surfaces or layers, for example, 107, configured in the throat and skin examination attachment 106, are configured to produce shadowless illumination without bright spots during the examination and the imaging of each of the organs, without requiring replacement of the stationary, multi-examination illumination unit 103 for the examination and the imaging of each of the organs.

In an embodiment, the multi-organ imaging system 100 further comprises a protective filter 108 configured to be coaxially positioned on the front end 106*a* of the throat and skin examination attachment 106 over the camera lens 102 and the stationary, multi-examination illumination unit 103. The attachment holder 105 holds the protective filter 108 and the throat and skin examination attachment 106 thereon. The protective filter 108 is configured to sit firmly at the front end 106*a* of the throat and skin examination attachment 106. In an embodiment, the protective filter 108 is configured to fit together with the front end 106*a* of the throat and skin examination attachment 106, for example, by screw threads. In another embodiment, the protective filter 108 is configured to fit together with the front end 106*a* of the throat and skin examination attachment 106, for example, by an annular snap-fit, or press-fit, or friction-fit attachment method. The protective filter 108 is a glass filter made, for example, from translucent or transparent glass, that attaches to the front end 106*a* of the throat and skin examination attachment 106. The protective filter 108 is configured to protect the camera lens 102 and the illuminators 104 of the stationary, multi-examination illumination unit 103, for example, from germs and particles of saliva produced in a patient's mouth during a throat examination. The illuminators 104 are positioned away from an optical axis passing through the camera body 101, at a distance from an outer edge of the protective filter 108. For example, through-hole or surface mount technology (SMT) light emitting diodes (LEDs) are placed moderately away from the optical axis than the edge of the protective filter 108. The camera lens 102 provides a field of view of, for example, about 100 mm at a distance of about 120 mm to a patient's mouth from the protective filter 108.

In an embodiment, the multi-organ imaging system 100 further comprises a display mounting member 112 operably coupled to and extending outwardly from the second end 101*b* of the camera body 101. In an embodiment, the display mounting member 112 is configured in a spherical shape for allowing movement of a display unit 125, for example, a tablet computing device, accommodated in a display holder 122 exemplarily illustrated in FIGS. 5A-5C, in multiple dimensions, for example, three dimensions, to achieve required ergonomics while aiming the camera lens 102 and visualizing the organs. The display mounting member 112 of the spherical shape is herein referred to as a "spherical mount". The display mounting member 112 is, for example, a ball configured to detachably attach to a clamping member 124, for example, a chuck, of the display holder 122 exemplarily illustrated in FIG. 5A.

In an embodiment, the multi-organ imaging system 100 further comprises a tool mounting member 115 attached to the first end 101a of the camera body 101, on the bottom section 100a of the multi-organ imaging system 100. The tool mounting member 115 is configured to mount and detachably attach a medical tool, for example, a tongue depressor 401 exemplarily illustrated in FIG. 4B, that allows an unobstructed view of one of the organs, for example, the throat, during the examination and the imaging of the organ. The medical tool is configured to set a distance between the multi-organ imaging system 100 and a target area of an organ being examined. The tool mounting member 115 also mounts and detachably attaches other medical tools, for example, attachments for a skin examination such as a skin attachment 402 exemplarily illustrated in FIG. 4C, and other medical examination procedures.

In an embodiment, the multi-organ imaging system 100 further comprises control elements 110a, 110b, and 110c positioned on the camera body 101. As exemplarily illustrated in FIG. 1, a control panel 109 comprising the control elements 110a, 110b, and 110c is positioned on and attached to the outer surface 101c of the camera body 101. Activation of the control elements 110a, 110b, and 110c triggers different functions. For example, activation of the control element 110a triggers a capture of a snapshot of a target area of one of the organs, for example, the throat or the skin, by the industrial camera unit 118 via the camera lens 102. In another example, the control elements 110b and 110c positioned on the outer surface 101c of the camera body 101 are light or illumination control buttons configured to adjust illumination settings, for example, brightness, of the stationary, multi-examination illumination unit 103. The control elements 110b and 110c control the intensity of illumination from the stationary, multi-examination illumination unit 103. Activation of the control element, for example, 110b or 110c, controls the brightness of the illumination produced by the illuminators 104 in the stationary, multi-examination illumination unit 103. In an embodiment, the control panel 109 comprising the control elements 110a, 110b, and 110c is positioned on a remote device (not shown) operably connected to the multi-organ imaging system 100 via a network. In another embodiment, the control element 110a that triggers the capture of a snapshot of a target area of an organ, for example, the throat, is a user interface element 126a, for example, a snap button, positioned on a graphical user interface (GUI) 126 of the display unit 125 as exemplarily illustrated in FIG. 5B. In another embodiment, the control element 110a that triggers the capture of a snapshot of a target area of an organ, for example, the throat, is positioned on a remote device (not shown) operably connected to the multi-organ imaging system 100 via a network. In an embodiment, the multi-organ imaging system 100 communicates the activation of the control element 110a to an operator of the multi-organ imaging system 100 via an audio signal.

In an embodiment, the multi-organ imaging system 100 further comprises a connector 113a, for example, a mating connector, positioned on the second end 101b of the camera body 101. The connector 113a is, for example, a universal serial bus (USB) 3.0 connector. The connector 113a is configured to connect a media and power cable 114, for example, a video and power cable, to the industrial camera unit 118 in the camera body 101 and transmit a media stream of each of the organs captured by the industrial camera unit 118 via the camera lens 102, to an external computing device 501 exemplarily illustrated in FIG. 5C, and to receive commands from the external computing device 501 with high data transfer speeds. The media and power cable 114 is, for example, a USB 3.0 cable. In this embodiment, the connector 113a connects the media and power cable 114 to the industrial camera unit 118 in the camera body 101 and transmits a media stream of the throat or the skin captured by the industrial camera unit 118 via the camera lens 102, to the external computing device 501, and receives commands from the external computing device 501.

Figure 2:
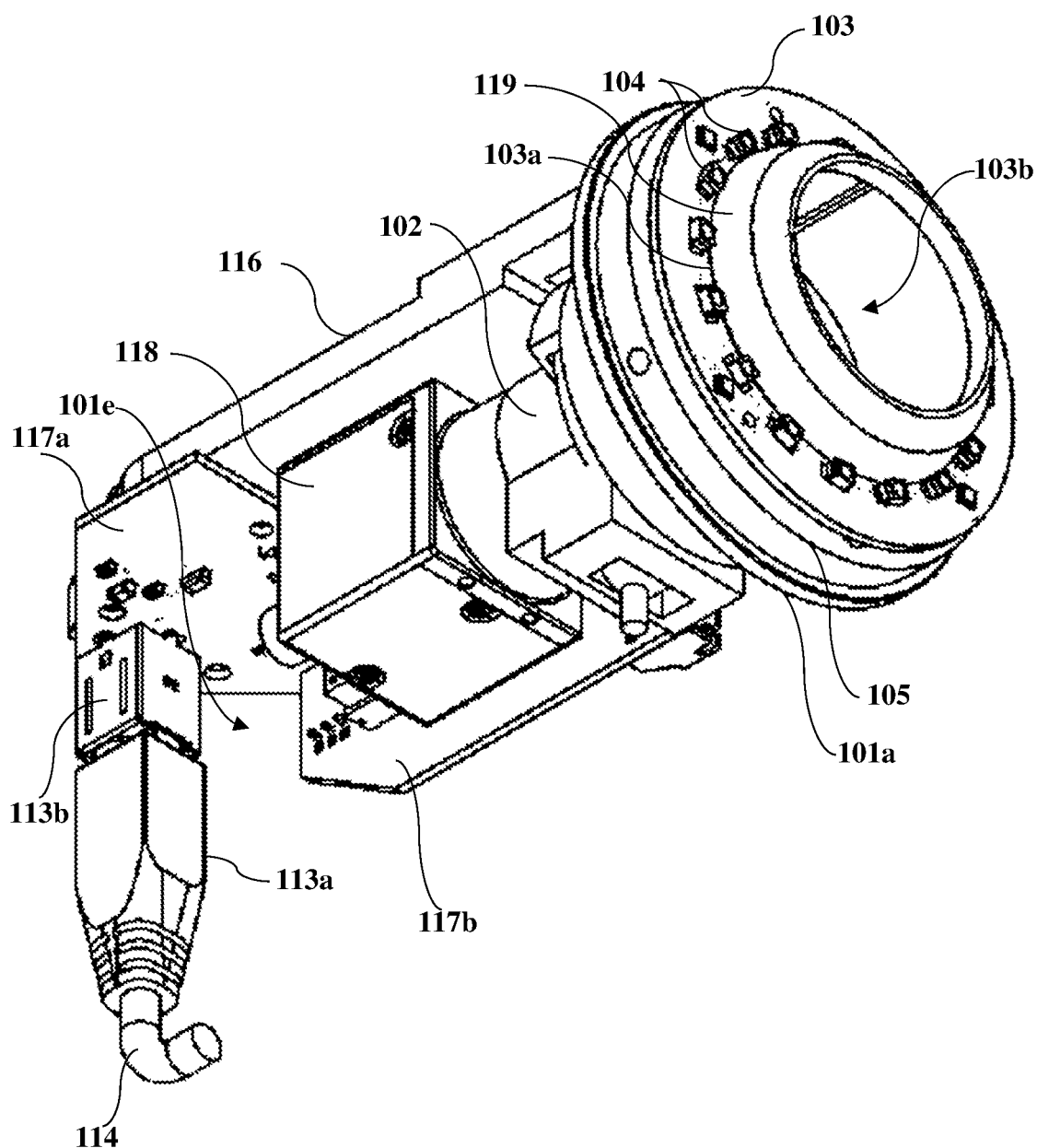
FIG. 2 exemplarily illustrates a cutaway, bottom perspective view of an embodiment of the multi-organ imaging system with the single, integrated, multi-examination illumination unit.

FIG. 2 exemplarily illustrates a cutaway, bottom perspective view of an embodiment of the multi-organ imaging system 100 with the single, integrated, multi-examination illumination unit 103. The camera body 101 of the multi-organ imaging system 100 exemplarily illustrated in FIG. 1, comprises a spine element 116 to which one or more components of the multi-organ imaging system 100 are attached and supported. For example, the display mounting member 112 is mechanically coupled to the spine element 116 of the camera body 101, and extends outwardly from the second end 101b of the camera body 101 as exemplarily illustrated in FIG. 1. In another example, a printed circuit board (PCB) 117a that houses image processing, storage, and transmission circuitry (IPSTC) of the multi-organ imaging system 100 is also attached to the spine element 116 of the camera body 101. In an embodiment, the spine element 116 also supports the industrial camera unit 118 within the camera body 101. As exemplarily illustrated in FIG. 2, the camera lens 102 is operably coupled to the industrial camera unit 118 within the camera body 101, for example, via a C-mount. The industrial camera unit 118 is positioned within the cavity 101e of the camera body 101 as exemplarily illustrated in FIG. 2. The industrial camera unit 118 comprises a sturdy housing that contains internal IPSTC, blocks electromagnetic emissions (EMEs), and protects the industrial camera unit 118, for example, from humidity, dust, and other environmental elements. In an embodiment, the IPSTC of the industrial camera unit 118 comprises, for example, a complementary metal-oxide-semiconductor (CMOS) image sensor or a charge coupled device (CCD) image sensor; a digital signal processor for creating and producing enhanced resolution image data and/or video data; a microcontroller for facilitating transmission of the image data and/or the video data to an external computing device 501 exemplarily illustrated in FIG. 5C; a universal serial bus (USB) 3.0/3.1, a gigabit Ethernet interface; a Power over Ethernet; CoaXPress interface; etc.

The industrial camera unit 118 consumes low power of, for example, about 2.5 watts (W), which results in low camera temperatures during medical examinations of a short duration. The industrial camera unit 118 is operably coupled to the camera lens 102, for example, via a C-mount. In an example, the industrial camera unit 118 comprises a complementary metal-oxide semiconductor (CMOS) sensor such as the IMX265 sensor of Sony Corporation having a sensor size of about 1/1.8 inches, a pixel size of about 3.45 micrometers (µm)×3.45 µm, a resolution of about 2048× 1536, a maximal frame rate of about 56 frames per second (fps), a USB 3.0, etc. The industrial camera unit 118 is enhanced with a pixel resolution of, for example, about 3 megapixels (MP) and a color depth of, for example, about 10 bits, for imaging multiple different organs, for example, ear, nose, throat, skin, eyes, etc. The industrial camera unit 118 converts optical signals into electrical signals, resulting in a digital image of an enhanced resolution and color depth.

The mating connector 113a outside the camera body 101 connects the media and power cable 114 to the industrial camera unit 118 via another mating connector 113b positioned inside the camera body 101. The mating connectors 113a and 113b are, for example, universal serial bus (USB)-B 3.0 connectors, that create a USB interface between the industrial camera unit 118 and an external computing device 501. The USB interface assists in transmitting the images captured by the industrial camera unit 118 via the camera lens 102 to the external computing device 501. The mating connector 113a outside the camera body 101 connects to the mating connector 113b inside the camera body 101 via a socket 101d configured at the second end 101b of the camera body 101 as exemplarily illustrated in FIG. 1. The mating connector 113a and the connected media and power cable 114 are in operable communication with the image processing, storage, and transmission circuitry in the industrial camera unit 118 via the printed circuit board (PCB) 117a attached to the spine element 116 inside the camera body 101 as exemplarily illustrated in FIG. 2.

In an embodiment, the image processing, storage, and transmission circuitry is mounted and configured on the PCBs 117a and 117b, external to the industrial camera unit 118 within the camera body 101. In an embodiment, the PCB 117a communicates data and power to the industrial camera unit 118 via a universal serial bus (USB) connection, for example, a USB 3.0 connection, provided by the mating connectors 113a and 113b, and taps some power for the stationary, multi-examination illumination unit 103. The multi-organ imaging system 100 is powered from an external power source through a USB connection, for example, the USB 3.0 connection provided by the mating connectors 113a and 113b. In an example, the multi-organ imaging system 100 receives about 4.5 W of power, where about 2.5 W is consumed by the industrial camera unit 118 and upto about 2 W is consumed by the stationary, multi-examination illumination unit 103. The PCB 117b houses the control elements 110a, 110b, and 110c of the control panel 109.

In an embodiment, the multi-organ imaging system 100 further comprises a light guard 119 positioned proximal to the camera lens 102 and the stationary, multi-examination illumination unit 103. In an embodiment, the light guard 119 is coaxially attached to an inner periphery 103a of the stationary, multi-examination illumination unit 103 as exemplarily illustrated in FIG. 2. The light guard 119 is configured to prevent reflection of light from the stationary, multi-examination illumination unit 103 into the camera lens 102. In an embodiment, the light guard 119 is configured to prevent reflection of light from the stationary, multi-examination illumination unit 103 and the protective filter 108 exemplarily illustrated in FIG. 1, into the camera lens 102. In an embodiment as exemplarily illustrated in FIG. 2, the stationary, multi-examination illumination unit 103 is configured as a ring-shaped PCB with the illuminators 104 spaced apart in a circular configuration. The ring-shaped stationary, multi-examination illumination unit 103 comprises an opening 103b with a diameter of, for example, about 45 mm. The illuminators 104 of the stationary, multi-examination illumination unit 103 generate a large light output area that assists in producing shadowless illumination.

Figure 3:
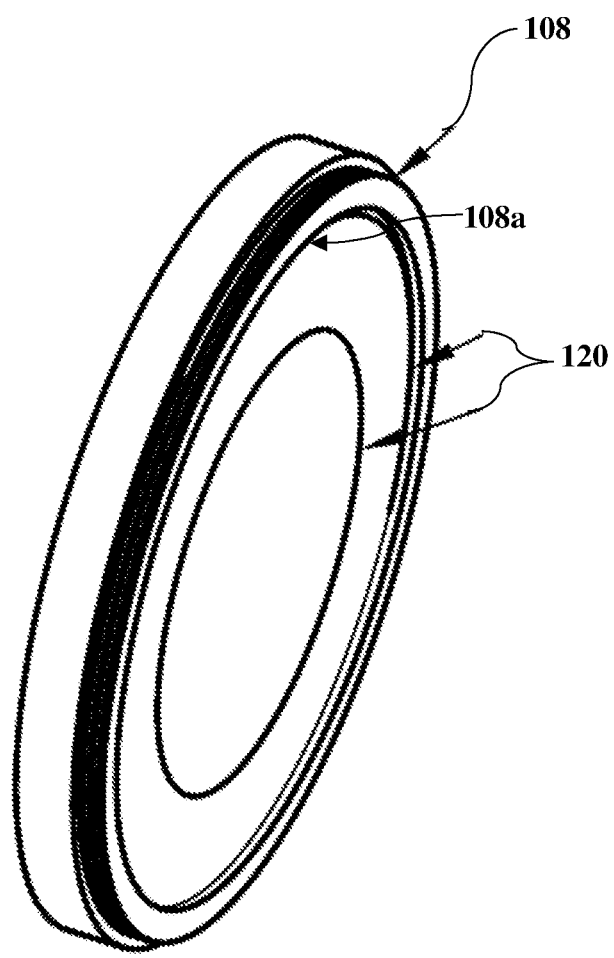
FIG. 3 exemplarily illustrates a perspective view of an embodiment of a protective filter with a light diffuser configured to protect a camera lens and illuminators of a stationary, multi-examination illumination unit.

FIG. 3 exemplarily illustrates a perspective view of an embodiment of a protective filter 108 with a light diffuser 120 configured to protect the camera lens 102 and the illuminators 104 of the stationary, multi-examination illumination unit 103. In an embodiment, in addition to protecting the camera lens 102 and the illuminators 104 of the stationary, multi-examination illumination unit 103, the protective filter 108 made, for example, of glass, also alters characteristics of light passing through the camera lens 102. In another embodiment, the protective filter 108 reduces ambient blue light. In an optional embodiment, the multi-organ imaging system 100 further comprises a light diffuser 120 coupled to an inner periphery 108a of the protective filter 108. The light diffuser 120 is configured to scatter light received from the illuminators 104 of the stationary, multi-examination illumination unit 103 for producing shadowless light for illuminating a target area of one of the organs. In an embodiment, the light diffuser 120 is a ring-shaped element as exemplarily illustrated in FIG. 3 and FIG. 4A. The light diffuser 120 reduces harsh shadows and balances lighting effects, creating soft light as disclosed in the detailed description of FIGS. 6A-6B. The light diffuser 120 is made, for example, from a translucent material, including ground glass, a polytetrafluoroethylene-based material such as Teflon®, opal glass, and greyed glass.

Figure 4A:
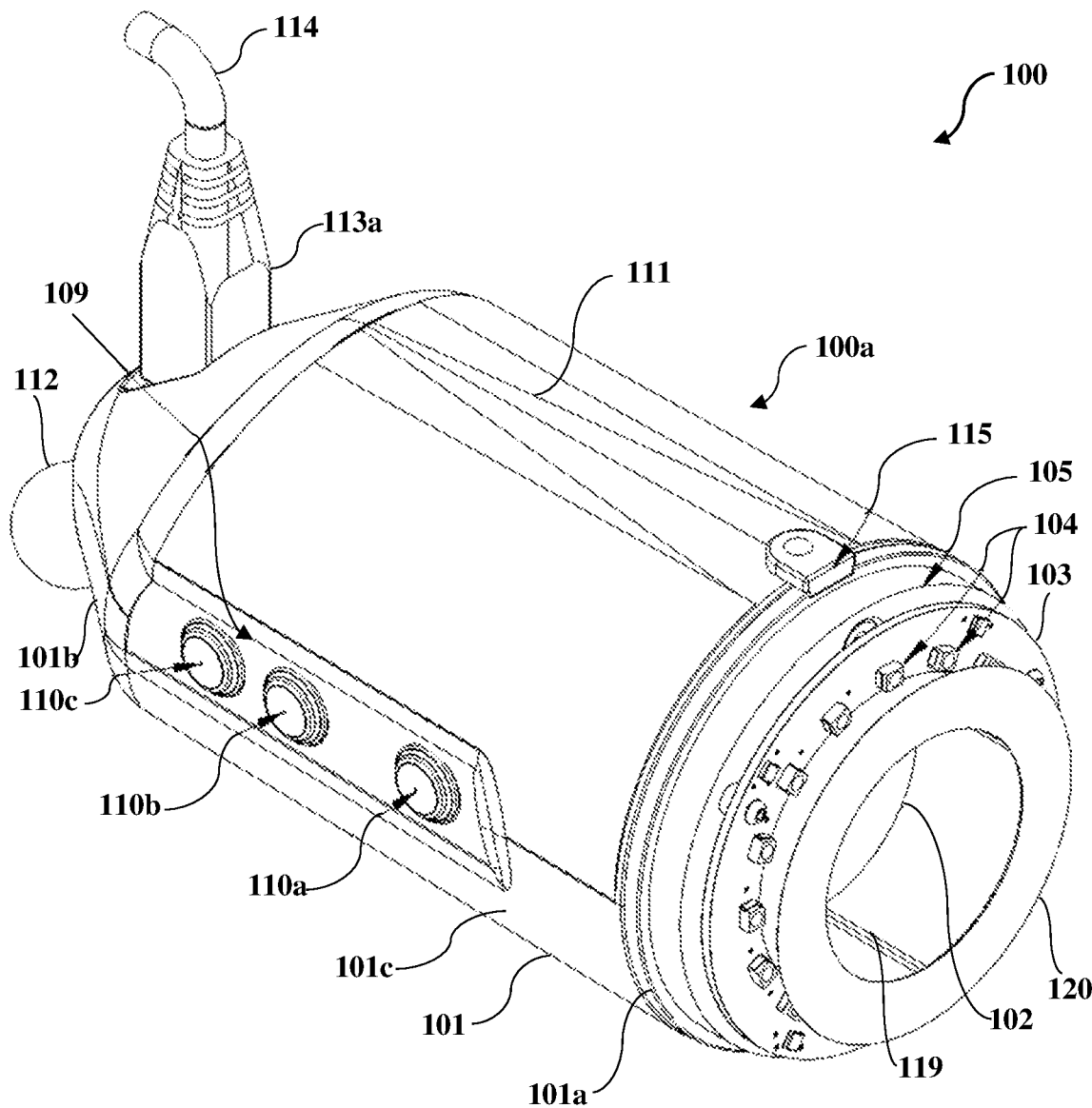
FIG. 4A exemplarily illustrates a perspective view showing a bottom section of the multi-organ imaging system with the single, integrated, multi-examination illumination unit shown in FIG. 1.

FIG. 4A exemplarily illustrates a perspective view showing a bottom section 100a of the multi-organ imaging system 100 with the single, integrated, multi-examination illumination unit 103 shown in FIG. 1. In FIG. 4A, the organ examination attachment, for example, the throat and skin examination attachment 106, and the protective filter 108 exemplarily illustrated in FIG. 1, are removed to expose the attachment holder 105; the stationary, multi-examination illumination unit 103 with its illuminators 104 arranged in a circular configuration; the light diffuser 120 positioned in front of the illuminators 104; the camera lens 102; and the light guard 119. As exemplarily illustrated in FIG. 4A, the light diffuser 120 is coaxially positioned over the camera lens 102 and in front of the stationary, multi-examination illumination unit 103. The light diffuser 120 scatters light received from the illuminators 104 of the stationary, multi-examination illumination unit 103 for producing shadowless light for illuminating a target area of one of the organs, for example, the throat, the skin, etc. The bottom section 100a of the multi-organ imaging system 100 comprises the tool mounting member 115 configured to mount and detachably attach a medical tool to the multi-organ imaging system 100 as disclosed in the detailed descriptions of FIGS. 4B-4C.

Figure 4B:
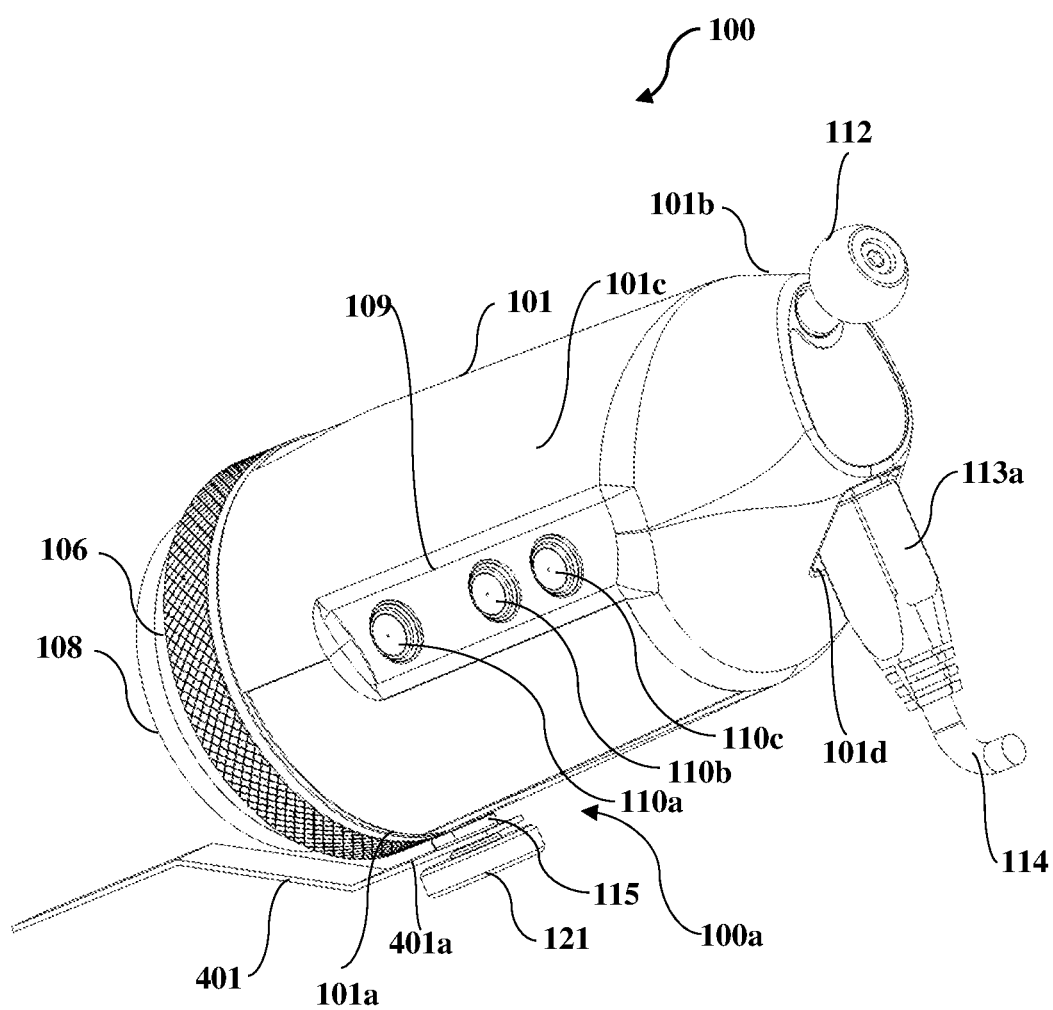
FIG. 4B exemplarily illustrates a rear perspective view of an embodiment of the multi-organ imaging system, showing a tongue depressor mounted and detachably attached to a tool mounting member of the multi-organ imaging system.

FIG. 4B exemplarily illustrates a rear perspective view of an embodiment of the multi-organ imaging system 100, showing a medical tool, for example, a tongue depressor 401, mounted and detachably attached to the tool mounting member 115 of the multi-organ imaging system 100. The tool mounting member 115 is attached to the first end 101a of the camera body 101 at the bottom section 100a of the multi-organ imaging system 100. The tool mounting member 115 is configured to mount and detachably attach the tongue depressor 401 to the multi-organ imaging system 100. The tongue depressor 401 is attached to the tool mounting member 115 of the multi-organ imaging system 100 using a fastener, for example, a thumb screw 121. In an embodiment (not shown), the tool mounting member 115 is configured as a slide-in mount on the bottom section 100a of the multi-organ imaging system 100 for sliding and securing an end section 401a of the tongue depressor 401 to the bottom section 100a of the multi-organ imaging system 100. In another embodiment, other mounts are used for attaching the tongue depressor 401 to the bottom section 100a of the multi-organ imaging system 100. During a throat examination, an operator of the multi-organ imaging system 100 depresses a patient's tongue using the attached tongue depressor 401 to obtain an unobstructed view of the patient's throat for examining and imaging the patient's throat using the multi-organ imaging system 100.

Figure 4C:
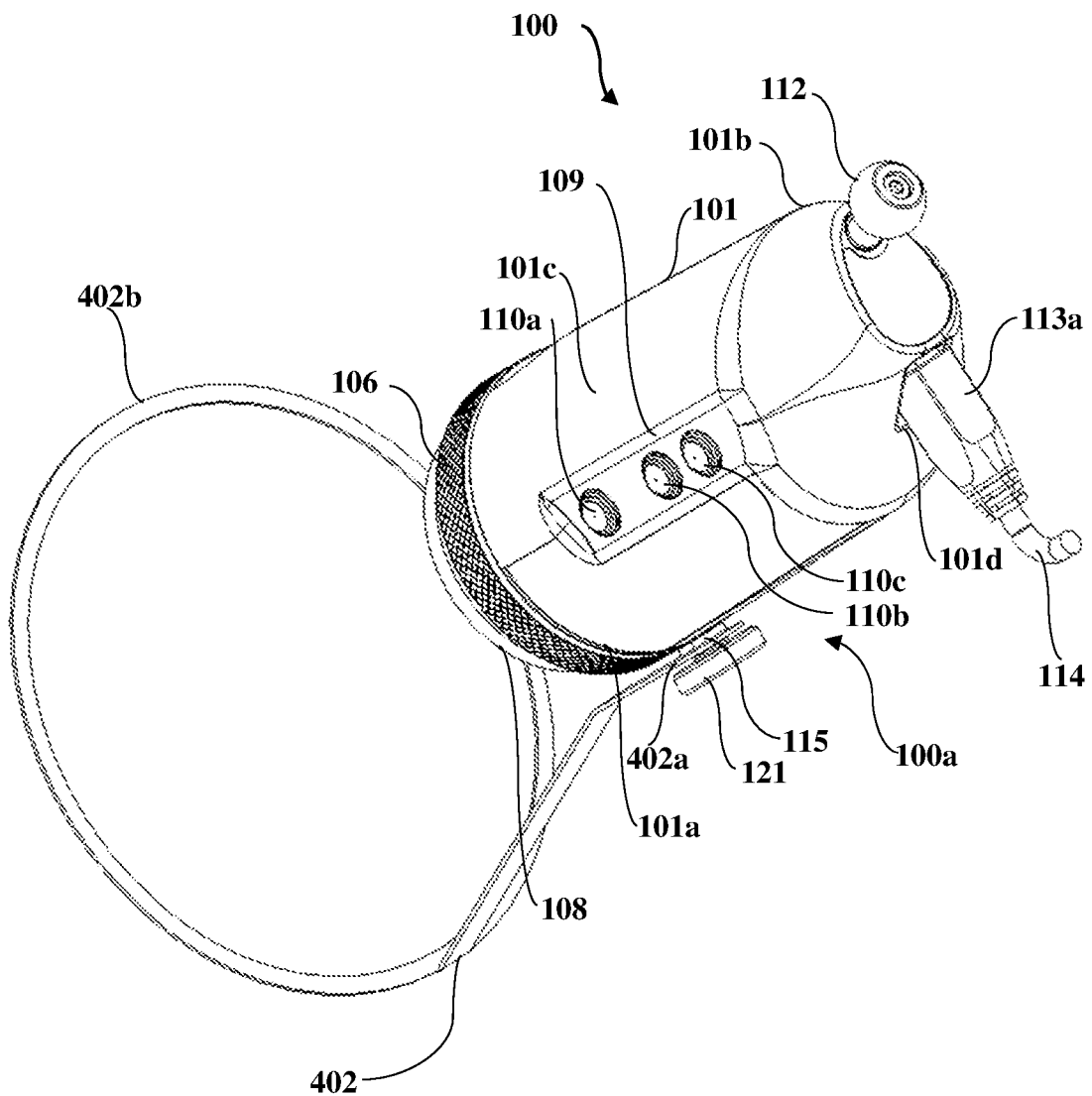
FIG. 4C exemplarily illustrates a rear perspective view of an embodiment of the multi-organ imaging system, showing a skin attachment mounted and detachably attached to a tool mounting member of the multi-organ imaging system.

FIG. 4C exemplarily illustrates a rear perspective view of an embodiment of the multi-organ imaging system 100, showing a medical tool, for example, a skin attachment 402, mounted and detachably attached to the tool mounting member 115 of the multi-organ imaging system 100. The tool mounting member 115 is attached to the first end 101a of the camera body 101 at the bottom section 100a of the multi-organ imaging system 100. The tool mounting member 115 is configured to mount and detachably attach the skin attachment 402 to the multi-organ imaging system 100. The skin attachment 402 is attached to the tool mounting member 115 of the multi-organ imaging system 100 using a fastener, for example, a thumb screw 121. In an embodiment (not shown), the tool mounting member 115 is configured as a slide-in mount on the bottom section 100a of the multi-organ imaging system 100 for sliding and securing an end section 402a of the skin attachment 402 to the bottom section 100a of the multi-organ imaging system 100. In another embodiment, other mounts are also used for attaching the skin attachment 402 to the bottom section 100a of the multi-organ imaging system 100. During a skin examination, an operator of the multi-organ imaging system 100 attaches an attachment element, for example, a ring-shaped element 402b, of the skin attachment 402 to a patient's skin to obtain an unobstructed view of the patient's skin for examining and imaging the patient's skin using the multi-organ imaging system 100. The skin attachment 402 allows positioning of the multi-organ imaging system 100 on a target area of the skin at a distance of, for example, about 120 mm, from the skin.

Figure 5A:
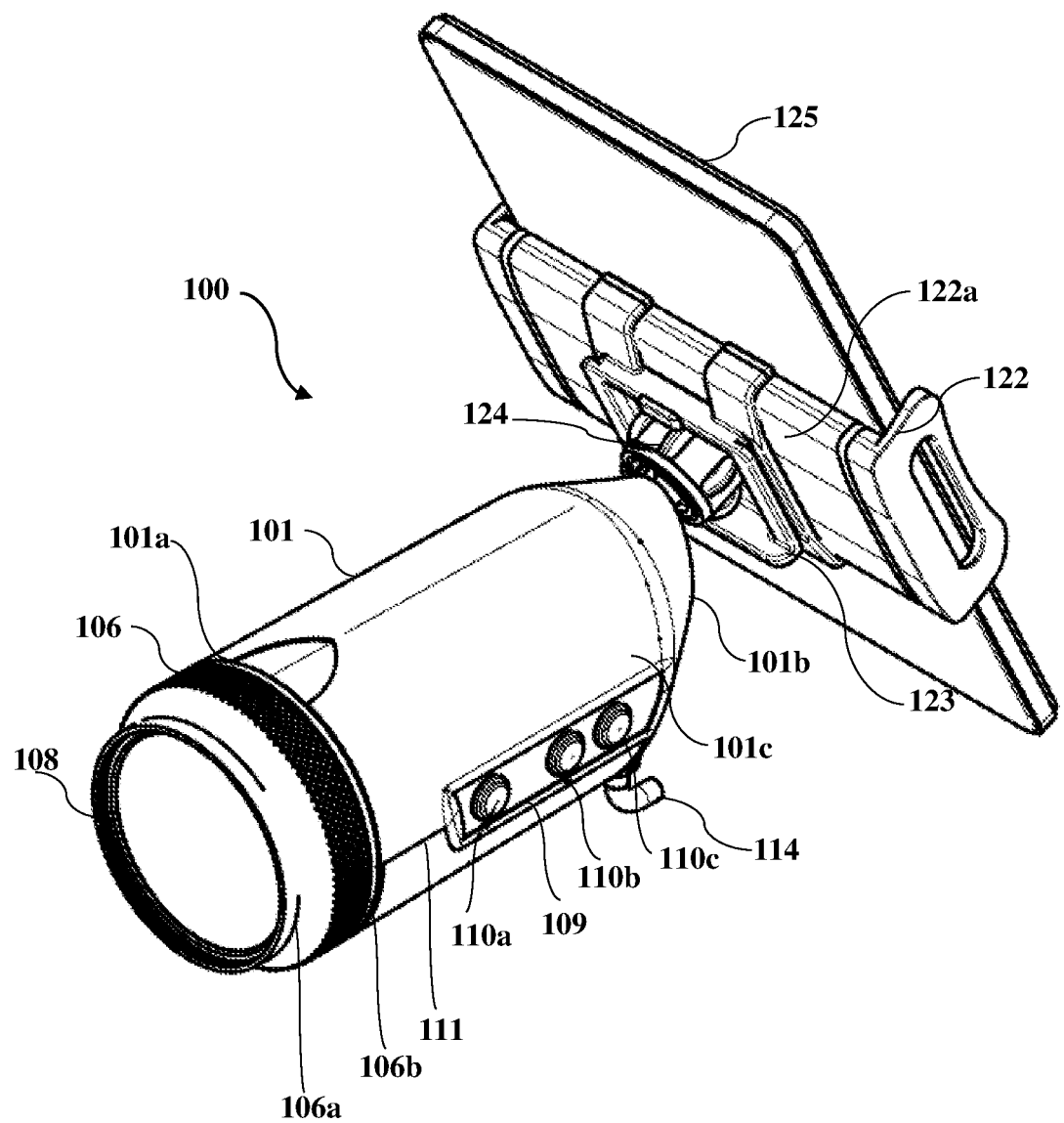
FIG. 5A exemplarily illustrates a top perspective view of an embodiment of the multi-organ imaging system, showing a display holder with a display unit detachably attached to a display mounting member of the multi-organ imaging system.

FIG. 5A exemplarily illustrates a top perspective view of an embodiment of the multi-organ imaging system 100, showing a display holder 122 with a display unit 125 detachably attached to the display mounting member 112 of the multi-organ imaging system 100. FIG. 5A illustrates an assembled view of the multi-organ imaging system 100 shown in FIG. 1. On assembly, the attachment holder 105 (not shown in FIG. 5A) coaxially accommodates the throat and skin examination attachment 106, such that the rear end 106b of the throat and skin examination attachment 106 sits firmly and securely at the first end 101a of the camera body 101. Furthermore, the protective filter 108 is coaxially positioned on the front end 106a of the throat and skin examination attachment 106. The display mounting member 112 is, for example, a ball of a spherical shape as exemplarily illustrated in FIG. 1 and FIGS. 4A-4C, and is herein referred to as a spherical mount 112. The spherical mount 112 allows movement of the display unit 125 accommodated in the display holder 122 in multiple dimensions, for example, three dimensions, to achieve required ergonomics while aiming the camera lens 102 and visualizing the organs, for example, the throat, the skin, etc. The spherical mount 112 extends outwardly from the second end 101b of the camera body 101 as exemplarily illustrated in FIG. 1 and FIGS. 4A-4C. The spherical mount 112 is attached to the spine element 116 of the camera body 101 exemplarily illustrated in FIG. 2, at the second end 101b of the camera body 101.

The display holder 122 securely accommodates the display unit 125, for example, a tablet computing device. The spherical mount 112 is configured to detachably attach to a clamping member 124, for example, a chuck, of the display holder 122. The clamping member 124 is securely attached to a rear surface 122a of the display holder 122 via a coupling mechanism 123 as exemplarily illustrated in FIG. 5A. The clamping member 124 of the display holder 122 is configured to accommodate and detachably engage with the spherical mount 112 positioned at the second end 101b of the camera body 101 for detachably attaching the display holder 122 and in turn, the display unit 125 accommodated therein, to the camera body 101. The clamping member 124 locks onto the spherical mount 112 and facilitates friction movement of the display holder 122 and in turn the display unit 125 accommodated therein. On engagement, the clamping member 124 of the display holder 122 holds the spherical mount 112 having a radial symmetry, and allows movement and proper positioning of the display unit 125 in multiple dimensions for viewing of a target area of an organ, for example, the throat or the skin, by an operator of the multi-organ imaging system 100. For purposes of illustration, the detailed description refers to the display mounting member 112 being a spherical mount, for example, a ball, configured to detachably attach to the clamping member 124, for example, a chuck, of the display holder 122, for detachably attaching the multi-organ imaging system 100 to the display holder 122, and in turn to the display unit 125 accommodated therein; however, the scope of the multi-organ imaging system 100 disclosed herein is not limited to the display mounting member 112 being a spherical mount and the clamping member 124 of the display holder 122 being a chuck, but may be extended to include different mating connectors that allow the detachable attachment of the multi-organ imaging system 100 to the display holder 122 and also the movement of the display holder 122 in multiple dimensions, for example, three dimensions, to achieve required ergonomics while aiming the camera lens 102 and visualizing organs, for example, the ear, the nose, the throat, the skin, the eyes, etc.

The display unit 125 accommodated in the display holder 122 is used for viewing a media feed captured by the industrial camera unit 118 via the camera lens 102 exemplarily illustrated in FIGS. 1-2. The display unit 125 assists in aiming the camera lens 102 and visualizing the organs. When the display holder 122 with the display unit 125 is attached to the multi-organ imaging system 100 comprising the throat and skin attachment 106 as exemplarily illustrated in FIG. 5A, the display unit 125 assists in aiming the camera lens 102 and visualizing the organs, for example, the throat, the skin, etc. The display unit 125 is configured to receive a media stream of each of the visualized organs, for example, the throat and the skin, captured by the industrial camera unit 118 via the camera lens 102. In an embodiment, the display unit 125 receives the media stream captured by the industrial camera unit 118 via the camera lens 102 from an external computing device 501 exemplarily illustrated in FIG. 5C, via a wired connection, for example, a universal serial bus (USB) connection. In another embodiment, the display unit 125 receives the media stream captured by the industrial camera unit 118 via the camera lens 102, from the external computing device 501 via a wireless connection 503 exemplarily illustrated in FIG. 5C, provided by a wireless network, for example, a communication network that implements Bluetooth® of Bluetooth Sig, Inc., a network that implements Wi-Fi® of Wi-Fi Alliance Corporation, etc.

In another embodiment, the industrial camera unit 118 is configured to broadcast the media stream on a wireless network, for example, a Bluetooth® network, a Wi-Fi® network, etc., to the display unit 125 and the external computing device 501. In this embodiment, the display unit 125 and the external computing device 501 receive the media stream directly from the industrial camera unit 118 via a wireless connection defined by a wireless communication protocol, for example, a Bluetooth® communication protocol, a Wi-Fi® communication protocol, etc. In another embodiment, the industrial camera unit 118 is connected to the display unit 125 via a wired connection, for example, a USB 3.0 cable connection. In this embodiment, the display unit 125 receives the media stream directly from the industrial camera unit 118 and transmits the media stream to the external computing device 501 via a wired connection, for example, a USB 3.0 cable connection, or via a wireless connection 503 defined by a wireless communication protocol, for example, a Bluetooth® communication protocol, a Wi-Fi® communication protocol, etc.

Figure 5B:
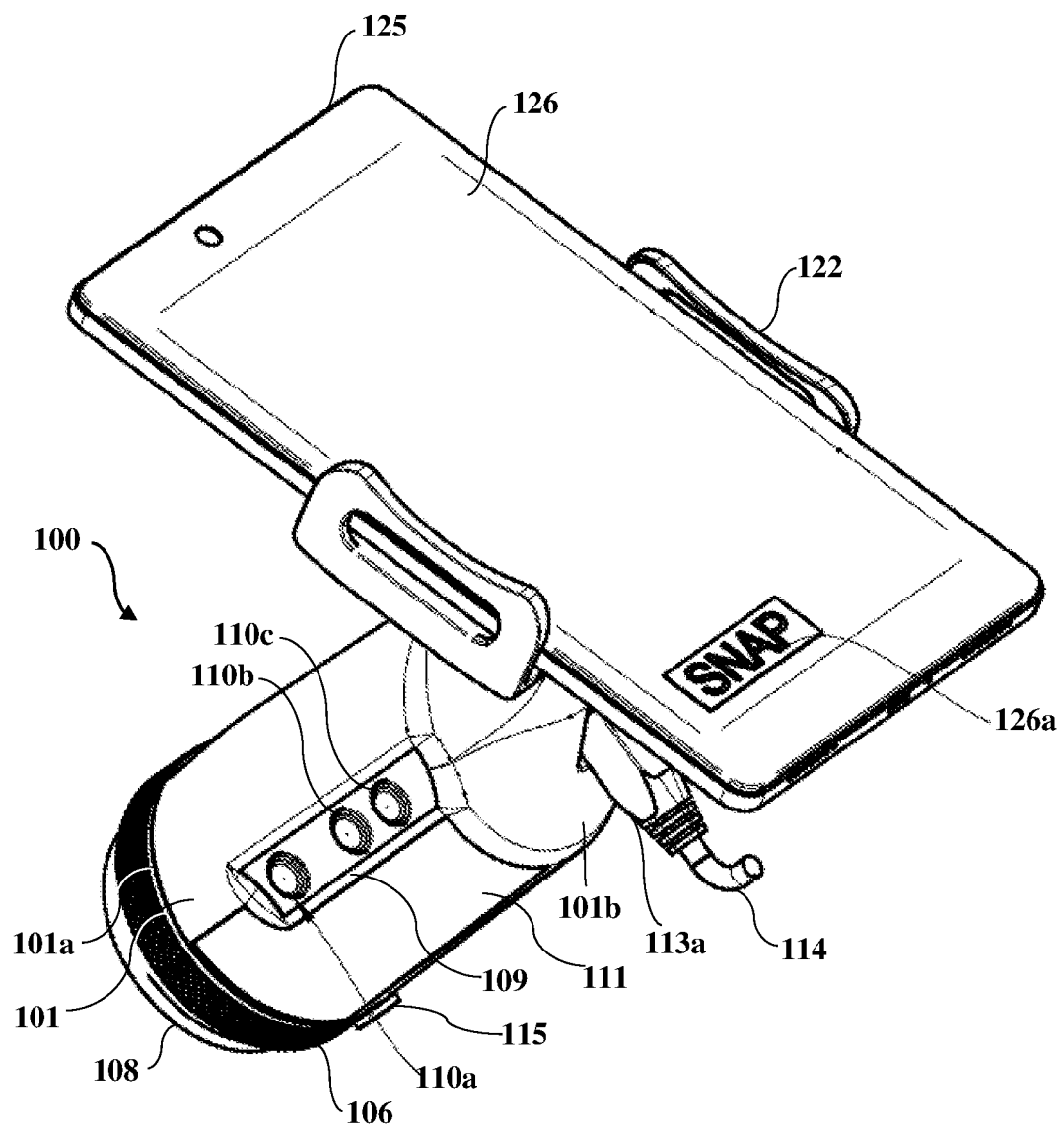
FIG. 5B exemplarily illustrates a rear perspective view of the multi-organ imaging system shown in FIG. 5A, showing the display holder with the display unit detachably attached to the multi-organ imaging system.
Figure 5C:
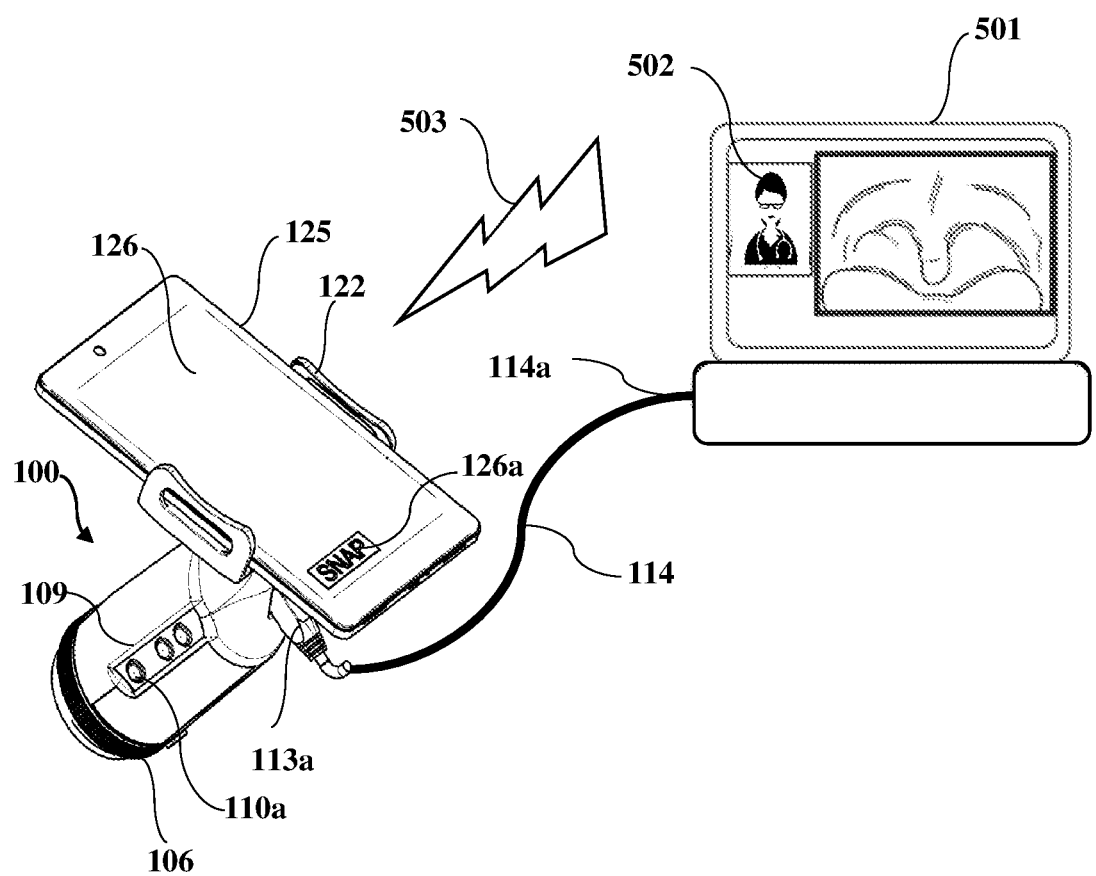
FIG. 5C exemplarily illustrates connection of an embodiment of the multi-organ imaging system to an external computing device.

The industrial camera unit 118, in optical communication with the camera lens 102, is configured to capture and display images of a target area of one of the organs, for example, the throat or the skin, using a control element 126a, for example, a snap button exemplarily illustrated in FIG. 5B. The industrial camera unit 118 is configured to store multiple imaging parameters that are invoked at activation or power up of the multi-organ imaging system 100. The imaging parameters comprise, for example, a predefined standard red, green, and blue (RGB) gamma value of about 0.4545, front light illumination, front light compensation, daylight color balance, auto white balance, fixed white balance, auto exposure such as brightness and contrast, optional image sharpening, etc. In an embodiment, the display unit 125 is detachable for compact storage, after examination. In an embodiment, the display unit 125 receives a copy of the media stream, for example, a video stream, from the industrial camera unit 118. The display unit 125 assists an operator of the multi-organ imaging system 100, for example, a health care worker, to aim the multi-organ imaging system 100 during examination and provides video feedback to the health care worker.

FIG. 5B exemplarily illustrates a rear perspective view of the multi-organ imaging system 100 shown in FIG. 5A, showing the display holder 122 with the display unit 125 detachably attached to the multi-organ imaging system 100. The display unit 125 is, for example, a tablet computing device comprising a graphical user interface (GUI) 126. In an embodiment, a control element 126a, for example, a snap button, is configured as a user interface element positioned on the GUI 126 of the display unit 125. When an operator of the multi-organ imaging system 100 activates the control element 126a, for example, by clicking or touching the control element 126a on the GUI 126, the industrial camera unit 118 via the camera lens 102 exemplarily illustrated in FIGS. 1-2, captures a snapshot of a target area of one of the organs, for example, the throat or the skin. In an embodiment, the multi-organ imaging system 100 communicates the activation of the control element 126a, and in turn, the capture of the snapshot, to the operator via an audio signal.

FIG. 5C exemplarily illustrates connection of an embodiment of the multi-organ imaging system 100 to an external computing device 501. In an embodiment, the multi-organ imaging system 100 is connected to the external computing device 501, for example, a desktop computer, a workstation, etc., via a wired connection provided by the media and power cable 114, for example, a universal serial bus (USB) 3.0 cable. One end 114a of the media and power cable 114 connects to a connector interface, for example, a USB 3.0 port, configured on the external computing device 501, thereby allowing transmission of captured images or a media stream, for example, a video stream, from the multi-organ imaging system 100 to the external computing device 501 via the connector 113a and the media and power cable 114. In an embodiment, the external computing device 501 can be, for example, any one of a personal computer, a tablet computing device, a mobile computer, a mobile phone, a smart phone, a portable computing device, a laptop, a personal digital assistant, a wearable computing device such as smart glasses, smart watches, etc., a touch centric device, a workstation, a server, a client device, a portable electronic device, a network enabled computing device, an interactive network enabled communication device, a television, another image capture device, etc. In an embodiment, the multi-organ imaging system 100 communicates with the external computing device 501 via the media and power cable 114 and transmits the media stream captured by the industrial camera unit 118 via the camera lens 102 exemplarily illustrated in FIGS. 1-2, to the external computing device 501 via the media and power cable 114. In an embodiment, the external computing device 501 transmits a copy of the captured images or the media stream received from the multi-organ imaging system 100 via the media and power cable 114, to the display unit 125 accommodated in the display holder 122 via a wireless connection 503 provided by a wireless network, for example, a communication network that implements Bluetooth® of Bluetooth Sig, Inc., a network that implements Wi-Fi® of Wi-Fi Alliance Corporation, etc. In another embodiment, the external computing device 501 transmits the copy of the captured images or the media stream to the display unit 125 in the display holder 122 via a wired connection, for example, a universal serial bus (USB) connection.

An operator of the multi-organ imaging system 100 may trigger the industrial camera unit 118 of the multi-organ imaging system 100 exemplarily illustrated in FIG. 2, to capture a snapshot or a video of an organ, for example, a patient's throat or skin, by either pressing a button, that is, the control element 110a on the control panel 109 of the multi-organ imaging system 100, or by clicking a virtual snap button, that is, that the control element 126a on the graphical user interface 126 of the display unit 125. In an embodiment, another health care worker 502 at a remote site may trigger the industrial camera unit 118 to capture a snapshot or a video of the organ, for example, by either pressing a button on a remote control panel positioned at the remote site during a diagnostic session. In an embodiment, the multi-organ imaging system 100 and/or the external computing device 501 are configured to communicate with a remote device at the remote site via a network, example, one of the internet, satellite internet, an intranet, a wired network, a wireless network, a Bluetooth® communication network, a Wi-Fi® network, an ultra-wideband (UWB) communication network, a wireless universal serial bus (USB) communication network, a communication network that implements ZigBee® of ZigBee Alliance Corporation, a general packet radio service (GPRS) network, a mobile telecommunication network such as a global system for mobile (GSM) communications network, a code division multiple access (CDMA) network, a fourth generation (4G) mobile communication network, a fifth generation (5G) mobile communication network, a long-term evolution (LTE) mobile communication network, a public telephone network, etc., a local area network, a wide area network, an internet connection network, an infrared communication network, etc., or a network formed from any combination of these networks. The remote device of the health care worker 502 at a remote site communicates a control signal from the remote control panel to the external computing device 501 via the network, and in turn to the industrial camera unit 118 via the media and power cable 114.

The external computing device 501 comprises a non-transitory, computer-readable storage medium having embodied thereon, computer program codes comprising instructions executable by at least one processor for implementing the following functionalities: an image processing functionality for receiving and processing the images generated by the image processing, storage, and transmission circuitry (IPSTC) operating in the industrial camera unit 118 exemplarily illustrated in FIG. 2; an image display functionality for displaying the processed images; an image capture functionality for capturing the displayed images; and an image management functionality for managing the captured images. In another embodiment, the functionalities implemented by the processor comprise a remote control functionality for remote control of the IPSTC. In another embodiment, the functionalities implemented by the processor comprise an image analysis functionality for analyzing the captured images. As used herein, "non-transitory, computer-readable storage medium" refers to all computer-readable media that contain and store computer programs and data, except for a transitory, propagating signal. Examples of the computer-readable media comprise hard drives, solid state drives, optical discs or magnetic disks, memory chips, a read-only memory (ROM), a register memory, a processor cache, a random-access memory (RAM), etc. In an embodiment, the captured images or the media streams are stored in a secure cloud storage platform.

Figure 6A:
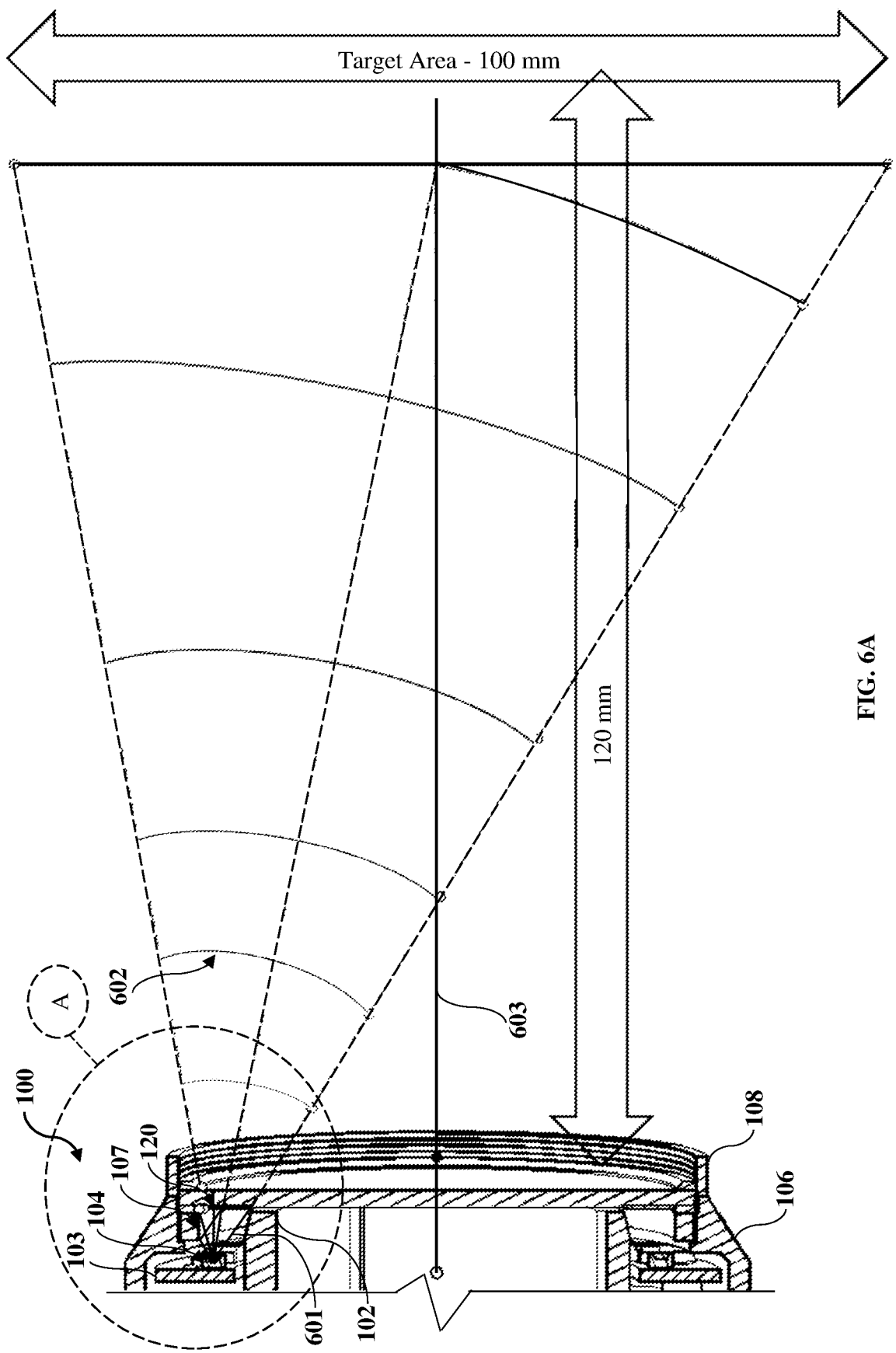
FIG. 6A exemplarily illustrates a partial cross-sectional view of an embodiment of the multi-organ imaging system, showing diffusion of light received from the stationary, multi-examination illumination unit, by a light diffuser, for producing shadowless light for illuminating a target area.

FIG. 6A exemplarily illustrates a partial cross-sectional view of an embodiment of the multi-organ imaging system 100, showing diffusion of light received from the stationary, multi-examination illumination unit 103, by the light diffuser 120, for producing shadowless light for illuminating a target area of an organ. During a throat examination, when the multi-organ imaging system 100 with the throat and skin attachment 106 is powered on, the illuminators 104, for example, the surface mount technology (SMT) light emitting diodes (LEDs) of the stationary, multi-examination illumination unit 103, emit light beams 601 towards a focusing and cover area, that is, a target area having a diameter of, for example, about 100 mm, in a patient's mouth. The distance between diametrically opposite illuminators 104 is, for example, about 60 mm for a protective filter 108 with a diameter of about 62 mm.

The stationary, multi-examination illumination unit 103 transmits direct light beams 601 into the patient's mouth. The direct light beams 601 produce a strong reflection from wet skin inside the patient's mouth. The stationary, multi-examination illumination unit 103 directs the light beams 601 at a wider angle to an optical axis 603, combining straight and reflected beams that are further diffused by the light diffuser 120. The illuminators 104 of the stationary, multi-examination illumination unit 103 are positioned further away from the camera lens 102 half hidden by an edge of the protective filter 108 to produce a wider striking angle. The light beams 601 emitted by the illuminators 104 strike the light diffuser 120 directly. In an embodiment, the reflective layer 107 reflects the light beams 601 onto the light diffuser 120. The light diffuser 120 scatters the direct and reflected light beams 601 for producing shadowless light for illuminating the target area. The scattered or diffused light 602 from the light diffuser 120 strikes and illuminates a target area of, for example, about 100 mm diameter, in the patient's mouth, when the multi-organ imaging system 100 is positioned at a distance of, for example, about 120 mm, from the target area as exemplarily illustrated in FIG. 6A.

Figure 6B:
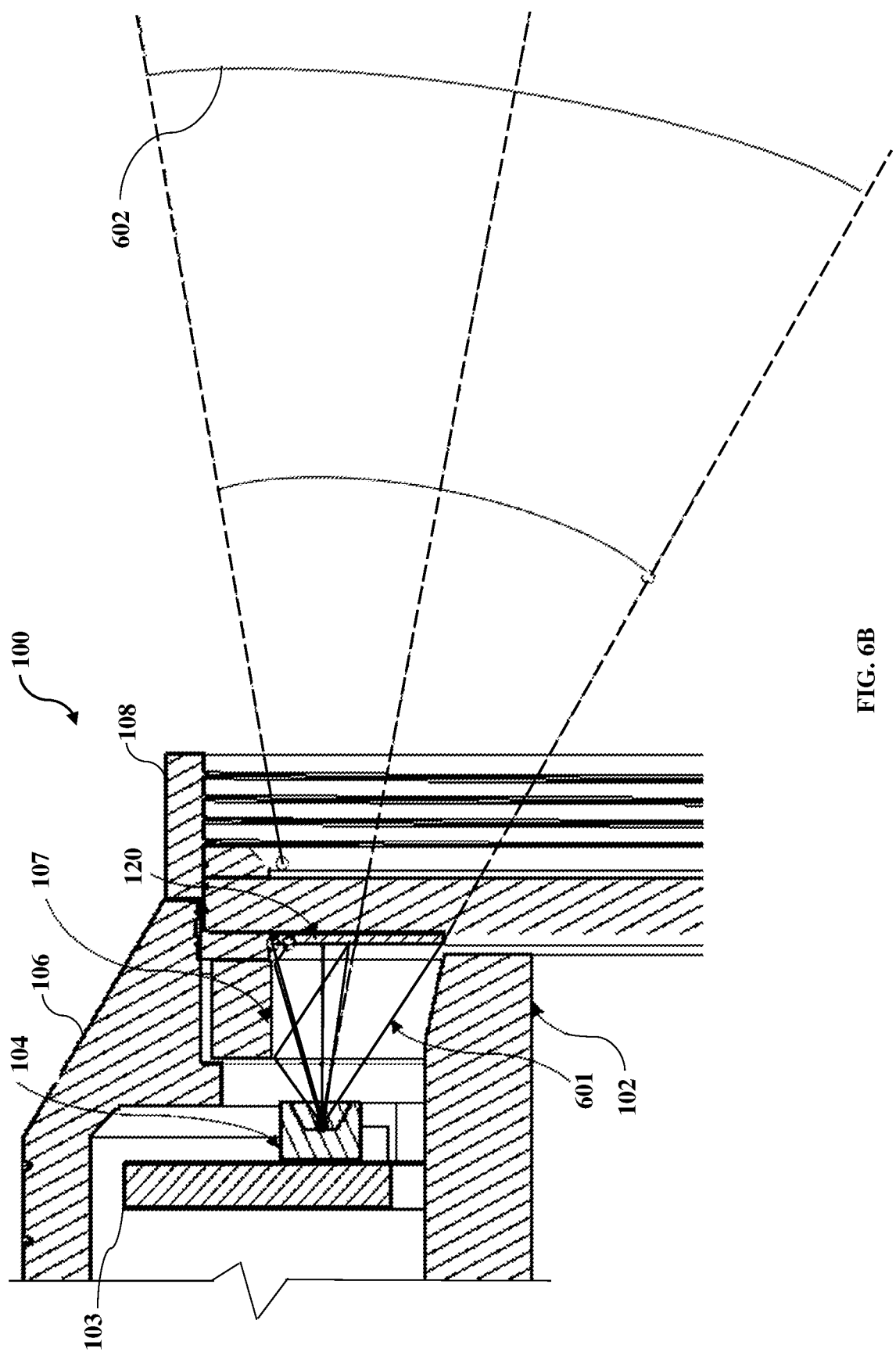
FIG. 6B exemplarily illustrates an enlarged view of a portion marked A of the multi-organ imaging system shown in FIG. 6A.

FIG. 6B exemplarily illustrates an enlarged view of a portion marked A of the multi-organ imaging system 100 shown in FIG. 6A. The light diffuser 120 emits the light beams 601 received from the illuminators 104 of the stationary, multi-examination illumination unit 103, from a uniform circular surface. The light behind the light diffuser 120 is uniform. The diffused light 602 directed towards the target area of, for example, about 100 mm diameter, is exemplarily illustrated in FIGS. 6A-6B.

Figure 7:
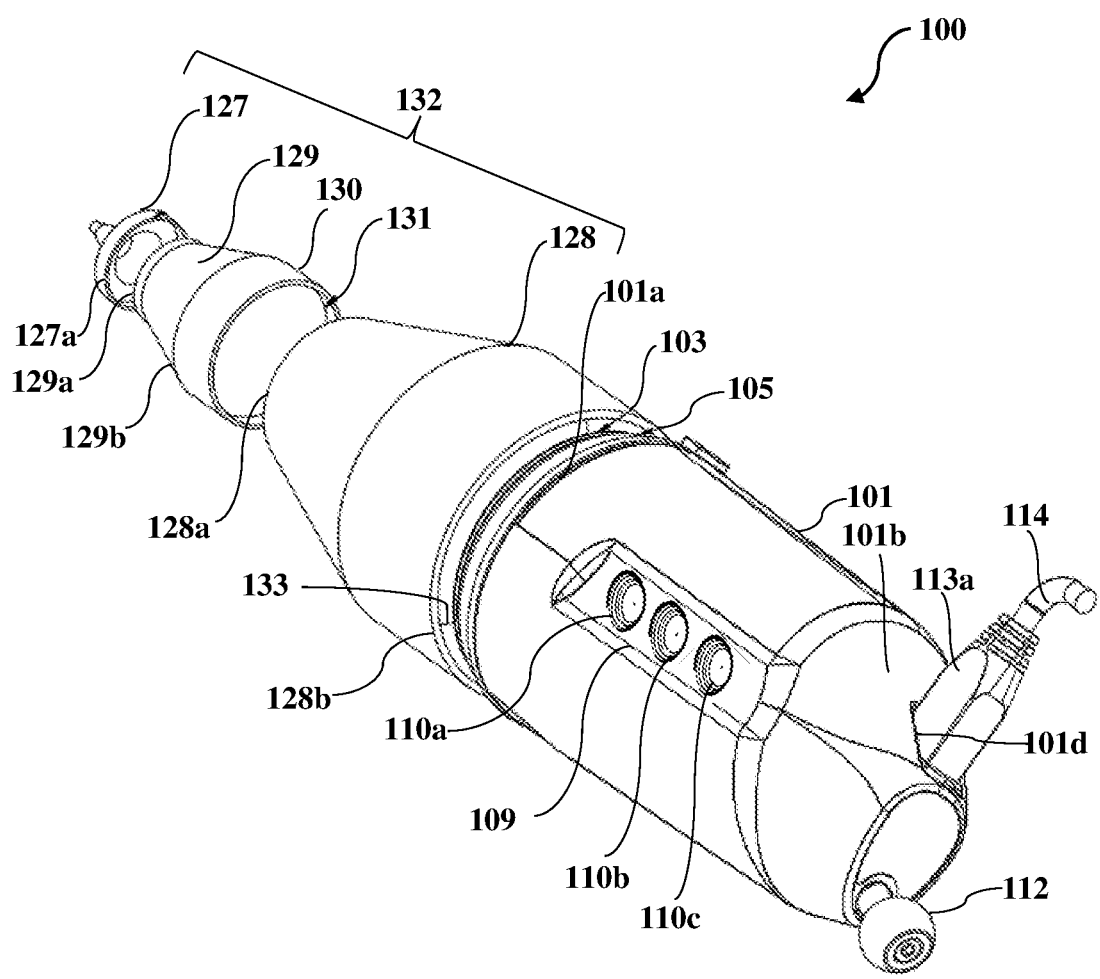
FIG. 7 exemplarily illustrates an exploded, rear perspective view of an embodiment of the multi-organ imaging system with the single, integrated, multi-examination illumination unit for performing ear examination and imaging.

FIG. 7 exemplarily illustrates an exploded, rear perspective view of an embodiment of the multi-organ imaging system 100 with the single, integrated, multi-examination illumination unit 103 for performing ear examination and imaging. In an embodiment, the organ examination attachment is an otoscope attachment 132 comprising an otoscope support member 128, a focusing cone 129, and a speculum 127. The parts of the otoscope attachment 132, that is, the otoscope support member 128, the focusing cone 129, and the speculum 127 are made, for example, from stainless steel or plastic. The otoscope support member 128 is configured to be coaxially accommodated on the attachment holder 105. In an embodiment, the otoscope attachment 132 further comprises a light separator 133 positioned inside the otoscope support member 128, in front of the stationary, multi-examination illumination unit 103 as disclosed in the detailed description of FIG. 9B. The focusing cone 129 is configured to be attached to a front end 128a of the otoscope support member 128. In an embodiment, the focusing cone 129 comprises a lens holder 130 configured to accommodate a supplemental lens 131. The supplemental lens 131, in optical communication with the camera lens 102 in the camera body 101, is configured to change a focusing distance of the industrial camera unit 118 exemplarily illustrated in FIG. 2, to cover a predetermined depth of an ear channel. In an embodiment, the supplemental lens 131 is a magnifying lens configured to produce a magnified image of a target area of the ear channel, in communication with the camera lens 102 and the industrial camera unit 118. The speculum 127 is configured to be operably coupled to a front end 129a of the focusing cone 129 for examining the ear channel and allowing imaging of the ear channel by the industrial camera unit 118 via the camera lens 102 exemplarily illustrated in FIG. 2. The speculum 127 is a cone- or funnel-shaped attachment of the otoscope attachment 132, that is inserted into the ear canal to examine the eardrum. In an embodiment, the speculum 127 of the otoscope attachment 132 is inserted into a patient's mouth to examine surrounding tissues of a throat area.

In an embodiment as exemplarily illustrated in FIG. 7, a control panel 109 comprising the control elements 110a, 110b, and 110c are positioned on and attached to the outer surface 101c of the camera body 101. Activation of the control elements 110a, 110b, and 110c triggers different functions as disclosed in the detailed description of FIG. 1. For example, activation of the control element 110a triggers a capture of a snapshot of a target area of an organ, for example, the ear, by the industrial camera unit 118 via the camera lens 102. The multi-organ imaging system 100 communicates the activation of the control element 110a to an operator of the multi-organ imaging system 100, for example, via an audio signal. In another example, the control elements, for example, 110b and 110c positioned on the outer surface 101c of the camera body 101 are configured to adjust illumination settings, for example, brightness, etc., of the stationary, multi-examination illumination unit 103.

FIG. 7 further illustrates a spherical-shaped display mounting member 112, herein referred to as the spherical mount 112, extending outwardly from the second end 101b of the camera body 101. The spherical mount 112 is operably coupled to the spine element 116 of the camera body 101 as exemplarily illustrated in FIG. 2. A clamping member 124, for example, a chuck, of the display holder 122 exemplarily illustrated in FIG. 5A, detachably attaches to the spherical mount 112 of the multi-organ imaging system 100 for detachably attaching the multi-organ imaging system 100 to the display holder 122. The display holder 122 accommodates a display unit 125, for example, a tablet computing device exemplarily illustrated in FIGS. 5A-5C. In an embodiment, the clamping member 124 of the display holder 122 moves about the spherical mount 112 of the multi-organ imaging system 100 in multiple dimensions, for example, three dimensions, thereby allowing movement and proper positioning of the display unit 125 accommodated in the display holder 122 in multiple dimensions to achieve required ergonomics while aiming the camera lens 102 and visualizing an organ, for example, the ear, the throat, etc. This allows an operator of the multi-organ imaging system 100 to optimally view a target area of the organ, for example, the ear, the throat, etc. When the display holder 122 with the display unit 125 exemplarily illustrated in FIGS. 5A-5C, is attached to the multi-organ imaging system 100 comprising the otoscope attachment 132, the display unit 125 assists in aiming the camera lens 102 and visualizing organs, for example, the ear, the throat, etc. The display unit 125 receives a media stream of each of the visualized organs, for example, the ear, the throat, etc., captured by the industrial camera unit 118 via the camera lens 102, from an external computing device 501 exemplarily illustrated in FIG. 5C, via a wired connection or a wireless connection 503 as disclosed in the detailed descriptions of FIGS. 5A-5C. The industrial camera unit 118, in optical communication with the camera lens 102, is configured to capture and display images of a target area of an organ, for example, the ear, the throat, etc. The industrial camera unit 118 stores imaging parameters that are invoked at activation or power up of the multi-organ imaging system 100. The imaging parameters comprise, for example, a predefined standard red, green, and blue (RGB) gamma value of about 0.4545, front light illumination, front light compensation, daylight color balance, auto white balance, fixed white balance, auto exposure activation, optional image sharpening, etc.

FIG. 7 further illustrates a connector 113a, for example, a universal serial bus (USB) 3.0 connector, positioned on the second end 101b of the camera body 101. The connector 113a extends from the socket 101d configured at the second end 101b of the camera body 101. The connector 113a connects the media and power cable 114, for example, a USB 3.0 video and power cable, to the industrial camera unit 118 in the camera body 101, transmits a media stream of an organ, for example, the ear, captured by the industrial camera unit 118 via the camera lens 102, to an external computing device 501 exemplarily illustrated in FIG. 5C, and receives commands from the external computing device 501 with high data transfer speeds.

Figure 8:
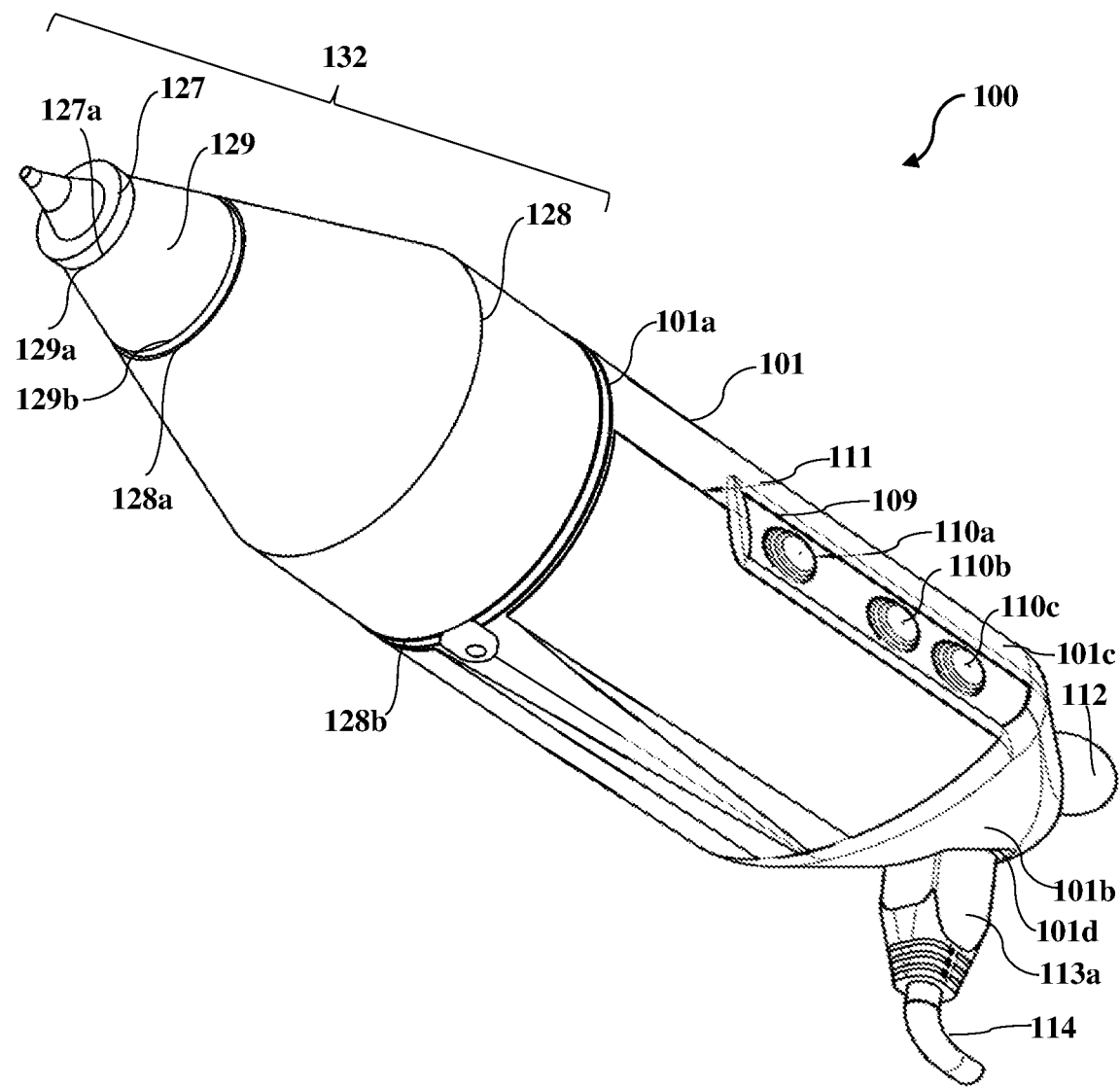
FIG. 8 exemplarily illustrates an assembled, bottom perspective view of the multi-organ imaging system shown in FIG. 7.

FIG. 8 exemplarily illustrates an assembled, bottom perspective view of the multi-organ imaging system 100 shown in FIG. 7. On assembly, the attachment holder 105 (not shown in FIG. 8) coaxially accommodates the otoscope attachment 132, such that the rear end 128b of the otoscope support member 128 of the otoscope attachment 132 sits firmly at the first end 101a of the camera body 101. The otoscope support member 128 is configured to fit together with the attachment holder 105, for example, by an annular snap-fit, or press-fit, or friction-fit attachment method, or by screw threads. Furthermore, the focusing cone 129 is coaxially positioned on the front end 128a of the otoscope support member 128, such that the rear end 129b of the focusing cone 129 sits firmly at the front end 128a of the otoscope support member 128. In an embodiment, the focusing cone 129 is configured to fit together with the otoscope support member 128, for example, by an annular snap-fit, or press-fit, or friction-fit attachment method, or by screw threads.

The lens holder 130 of the focusing cone 129 exemplarily illustrated in FIG. 7, extends inside the otoscope support member 128.

The speculum 127 is operably coupled to the front end 129a of the focusing cone 129 such that the rear end 127a of the speculum 127 sits firmly at the front end 129a of the focusing cone 129. The speculum 127 is configured to fit together with the focusing cone 129, for example, by an annular snap-fit, or press-fit, or friction-fit attachment method, or by screw threads. The speculum 127 is configured to allow visualization of the ear channel for examination and imaging of the ear channel by the industrial camera unit 118 via the camera lens 102 exemplarily illustrated in FIG. 2. The spherical mount 112 is attached to the spine element 116 of the camera body 101 exemplarily illustrated in FIG. 2, at the second end 101b of the camera body 101. The spherical mount 112 allows detachable attachment of the display holder 122 with the display unit 125, for example, a tablet computing device, to the camera body 101 using the clamping member 124, for example, a chuck, of the display holder 122 exemplarily illustrated in FIGS. 5A-5B. The media and power cable 114, via the connector 113a, transmits images or a media stream of the organ, for example, the ear, captured by the industrial camera unit 118 via the camera lens 102, to an external computing device 501 exemplarily illustrated in FIG. 5C, and receives commands from the external computing device 501 with high data transfer speeds.

Figure 9A:
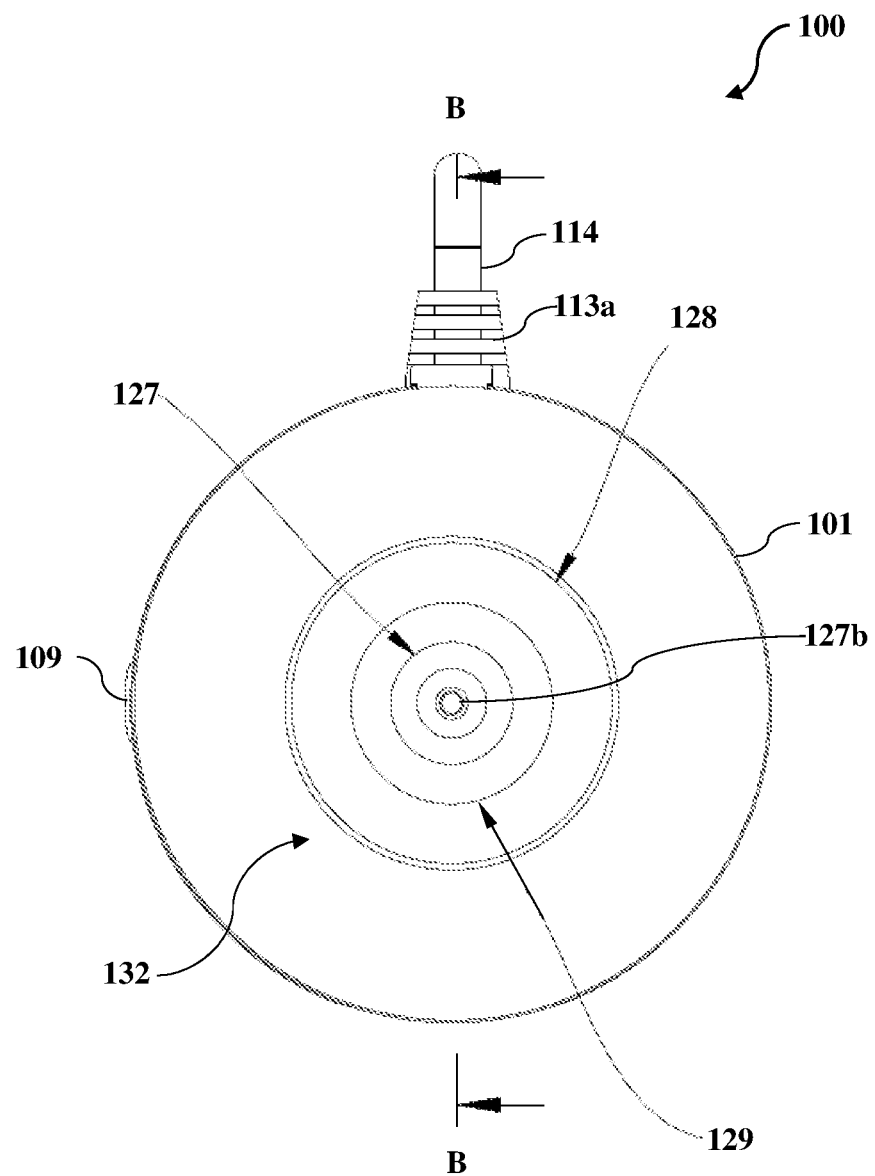
FIG. 9A exemplarily illustrates a front elevation view of the multi-organ imaging system shown in FIG. 8.

FIG. 9A exemplarily illustrates a front elevation view of the multi-organ imaging system 100 shown in FIG. 8. A tip 127b of the speculum 127 of the otoscope attachment 132 is exemplarily illustrated in FIG. 9A. The speculum 127 is a funnel-shaped device that allows examination of an eardrum and an ear canal. An operator of the multi-organ imaging system 100, for example, a health care worker, inserts the tip 127b of the speculum 127 into the ear to examine the ear using the display unit 125 accommodated in the display holder 122, which is detachably attached to the display mounting member, for example, the spherical mount 112, using the clamping member 124 exemplarily illustrated in FIGS. 5A-5B. The connector 113a connects the media and power cable 114 to the industrial camera unit 118 in the camera body 101 as exemplarily illustrated in FIG. 2, transmits a media stream of the ear captured by the industrial camera unit 118 via the camera lens 102 exemplarily illustrated in FIG. 2, to an external computing device 501 exemplarily illustrated in FIG. 5C, and receives commands from the external computing device 501 with high data transfer speeds.

Figure 9B:
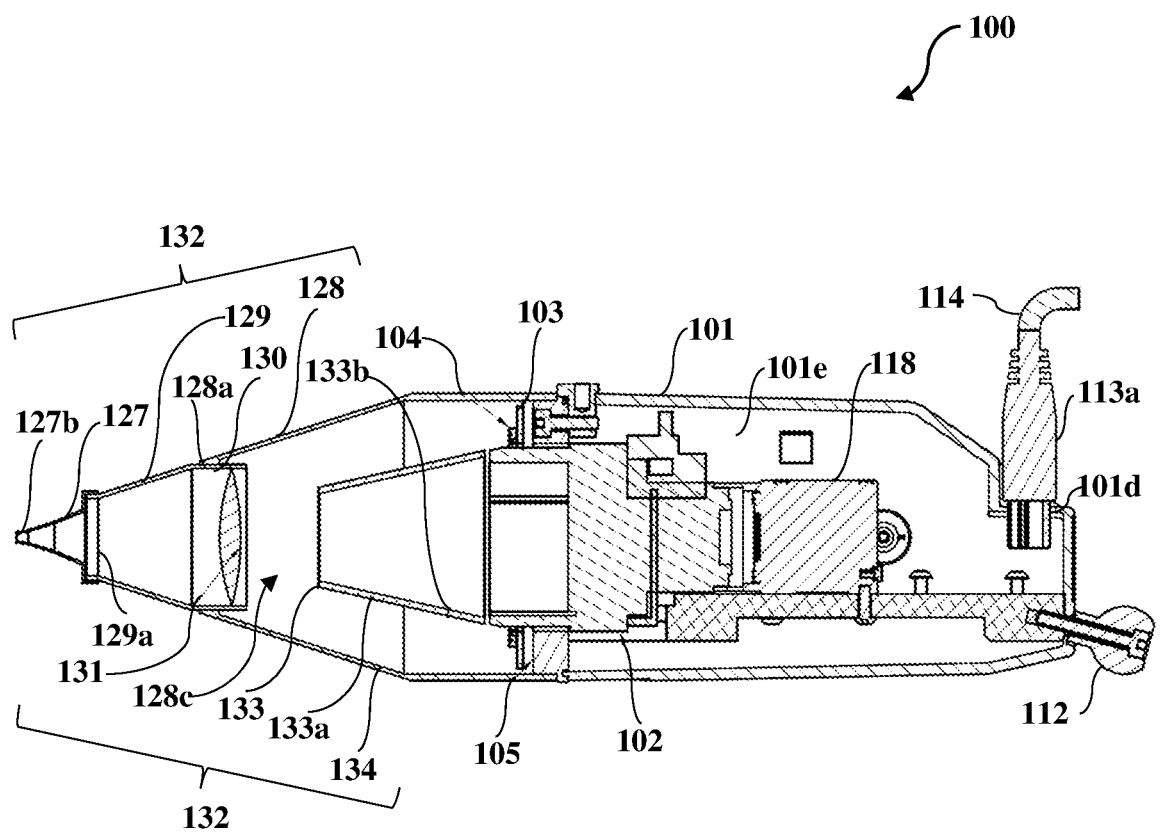
FIG. 9B exemplarily illustrates a cross-sectional view of the multi-organ imaging system, taken along a section B-B shown in FIG. 9A.

FIG. 9B exemplarily illustrates a cross-sectional view of the multi-organ imaging system 100, taken along a section B-B shown in FIG. 9A. As exemplarily illustrated in FIG. 9B, during assembly of the multi-organ imaging system 100, the otoscope support member 128 of the otoscope attachment 132 is coaxially accommodated on the attachment holder 105. In an embodiment, the otoscope support member 128 comprises a reflective inner surface 134. The focusing cone 129 of the otoscope attachment 132 is attached to the front end 128a of the otoscope support member 128, such that the lens holder 130 holding the supplemental lens 131 extends into a cavity 128c of the otoscope support member 128. The lens holder 130 comprises slits or cuts (not shown) configured to pass reflected light from the illuminators 104 towards the speculum 127 around the supplemental lens 131. The supplemental lens 131 is configured to change the focusing distance of the industrial camera unit 118 to cover the depth of the ear channel, for example, of about 10 millimeters (mm). The speculum 127 is operably coupled to the front end 129a of the focusing cone 129 for examining the ear channel. The speculum 127 allows visualization and imaging of the ear channel by the industrial camera unit 118 via the camera lens 102 exemplarily illustrated in FIG. 2.

In an embodiment, the light separator 133 of the otoscope attachment 132 is configured in the form of a light tunnel coupled with the stationary, multi-examination illumination unit 103. In an embodiment, the light separator 133 comprises one or more reflective outer surfaces 133a configured to form a light tunnel in optical communication with the reflective inner surface or layer 134 of the otoscope support member 128 and the stationary, multi-examination illumination unit 103 for assisting in the production of the shadowless illumination during the examination of the ear channel. The light tunnel is formed between two cones defined by the reflective outer surface 133a of the light separator 133 and the reflective inner surface 134 of the otoscope support member 128. In an embodiment, the light separator 133 further comprises a blackened inner surface 133b configured to absorb light reflections into the camera lens 102. Light reflected by the reflective surfaces 133a and 134 is concentrated into the tip 127b of the speculum 127 for illuminating the ear channel. In an embodiment, the stationary, multi-examination illumination unit 103 illuminates a target area of, for example, about 10 mm diameter, in the ear channel, when the tip 127b of the speculum 127 of the otoscope attachment 132 is positioned at a distance of, for example, about 24 mm, from the eardrum also referred to as the tympanic membrane. That is, the area of coverage is about 10 mm and the depth is about 24 mm from the tip 127b of the speculum 127.

The industrial camera unit 118, via the camera lens 102, captures images, for example, digital still images and/or digital video frames, of the target area of the patient's ear. The image processing, storage, and transmission circuitry (IPSTC) in the industrial camera unit 118 transmits the images to the external computing device 501 via the connector 113a and the media and power cable 114 exemplarily illustrated in FIG. 5C. In an embodiment, the display unit 125 in the display holder 122 receives a copy of the images from the external computing device 501, for example, via a wireless connection 503 defined, for example, by a Bluetooth® communication protocol or a Wi-Fi® communication protocol as exemplarily illustrated in FIG. 5C. In an embodiment, the IPSTC in the industrial camera unit 118 is configured to capture an image at least partially simultaneously with the image being viewable by a health care worker via the display unit 125. In another embodiment, the IPSTC is configured to store at least one of the digital still images and the digital video frames. In another embodiment, the IPSTC is configured to perform live video streaming of the image to the external computing device 501 in real time. In another embodiment, the IPSTC is operably disposed external to the industrial camera unit 118.

Consider an example of performing an examination of a patient's ear using the multi-organ imaging system 100. To perform an examination of a target area of the patient's ear, for example, the external auditory canal, the tympanic membrane or the eardrum, or the middle ear, a health care worker grips the camera body 101 of the multi-organ imaging system 100 and attaches the otoscope attachment 132 on the attachment holder 105 of the multi-organ imaging system 100. The health care worker also places the display unit 125 on the display holder 122 operably coupled to the spherical mount 112 of the multi-organ imaging system 100 using the clamping member 124 as exemplarily illustrated in FIGS. 5A-5B. When the multi-organ imaging system 100 is powered on using one of the control elements, for example, 110b or 110c, on the control panel 109 positioned on the camera body 101 as exemplarily illustrated in FIG. 8, the stationary, multi-examination illumination unit 103 is activated and the illuminators 104 of the stationary, multi-examination illumination unit 103 produce illumination and emit light towards the tip 127b of the speculum 127 coupled to the front end 129a of the focusing cone 129 of the otoscope attachment 132 exemplarily illustrated in FIG. 8.

The illuminators 104, in optical communication with one or more reflective surfaces, for example, 133a and 134, configured in the otoscope attachment 132 produce shadowless illumination without bright spots during the examination and the imaging of the ear. The emitted light reflects off the reflective outer surface 133a of the light separator 133 and the reflective inner surface 134 of the otoscope support member 128 exemplarily illustrated in FIG. 9B, thereby focusing the light towards the tip 127b of the speculum 127 and assisting in production of the shadowless illumination during the examination of an ear channel. The cone-shaped light separator 133 allows more light to be focused on the tip 127b of the speculum 127. The supplemental lens 131 is configured to change the focusing distance of the industrial camera unit 118 exemplarily illustrated in FIG. 9B, to cover, for example, a 10 mm depth of the ear channel. Furthermore, in an embodiment, the light separator 133 prevents reflection of light from the stationary, multi-examination illumination unit 103 and the protective filter 108 into the camera lens 102. At power up of the multi-organ imaging system 100, the industrial camera unit 118 is set with the following imaging parameters automatically: a standard red, green, and blue (RGB) gamma value of 0.4545, front light illumination, front light compensation, daylight color balance, auto white balance, fixed white balance, auto exposure activation, optional image sharpening, etc.

To perform the ear exam, the health care worker gently pulls the ear back and slightly up to straighten the ear canal. The health care worker inserts the tip 127b of the speculum 127 of the otoscope attachment 132 into the ear and gently moves the speculum 127 through the middle of the ear canal to avoid irritating the canal lining. When the health care worker inserts the tip 127b of the speculum 127 inside a patient's ear, the industrial camera unit 118, in operable communication with the camera lens 102 and the supplemental lens 131, captures an image or a video stream of the ear channel, which is illuminated by the stationary, multi-examination illumination unit 103. The display unit 125 assists the health care worker in aiming the camera lens 102 and visualizing the ear channel. When the health care worker touches or clicks on the control element 110a on the control panel 109 or the control element 126a such as the snap button displayed on the graphical user interface (GUI) 126 of the display unit 125 exemplarily illustrated in FIG. 5B, the industrial camera unit 118 via the camera lens 102 exemplarily illustrated in FIGS. 1-2, captures a snapshot or a video of the target area of the ear. In an embodiment, the multi-organ imaging system 100 communicates the activation of the control element 110a or 126a by providing an audio signal to the health care worker.

The health care worker may trigger the industrial camera unit 118 to capture a snapshot or a video, for example, by either pressing a button, that is, the control element 110a on the control panel 109 of the multi-organ imaging system 100, or by clicking a virtual button, that is, that control element 126a on the GUI 126 of the display unit 125 exemplarily illustrated in FIG. 5B. In an embodiment, another health care worker at a remote site may trigger the industrial camera unit 118 to capture a snapshot or a video, for example, by either pressing a button on a remote control panel positioned at the remote site during a diagnostic session. This remote control panel is operably connected to the external computing device 501 exemplarily illustrated in FIG. 5C, and in turn, to the multi-organ imaging system 100 via a network, for example, a long-range network or a short-range network. The health care worker at the remote site may obtain the snapshot of the target area by remotely connecting to the external computing device 501, and in turn, to the multi-organ imaging system 100 during the diagnostic session. The multi-organ imaging system 100 communicates any of the above disclosed button actions to the operator of the multi-organ imaging system 100, for example, by an audio signal.

The industrial camera unit 118 transmits the captured image or the video to the external computing device 501 via the connector 113a and the media and power cable 114 and further to the display unit 125 from the external computing device 501 via a wireless connection 503 defined by a wireless communication protocol exemplarily illustrated in FIG. 5C. The display unit 125 displays the captured image or the video without bright spots. After the examination is completed, the health care worker detaches the display holder 122 with the display unit 125 from the spherical mount 112 of the multi-organ imaging system 100 for compact storage. The health care worker may analyze the images or the video on the external computing device 501 at a later time. The copy of the captured image or the video stream shown on the display unit 125 assists the health care worker to aim the multi-organ imaging system 100 properly with the help of video feedback.

Consider an example of performing an examination of another organ, for example, a patient's throat using the multi-organ imaging system 100. To perform an examination of the throat, the health care worker grips the camera body 101 of the multi-organ imaging system 100, detaches the otoscope attachment 132 from the attachment holder 105, and mounts and attaches the throat and skin examination attachment 106 on the attachment holder 105 exemplarily illustrated in FIG. 1, without replacing the stationary, multi-examination illumination unit 103. The health care worker also places the display unit 125 on the display holder 122 operably coupled to the spherical mount 112 of the multi-organ imaging system 100 using the clamping member 124 as exemplarily illustrated in FIGS. 5A-5B. The health care worker requests the patient to open the mouth wide and positions the multi-organ imaging system 100 up to a predefined distance, for example, about 100 mm to about 150 mm, to the throat and aims the multi-organ imaging system 100 at the throat. The camera lens 102 of the multi-organ imaging system 100 exemplarily illustrated in FIGS. 1-2, provides a sharp whole mouth view when the multi-organ imaging system 100 is, for example, 120 mm from the throat, and covers a 100 mm width with a 60 mm depth in the mouth. The health care worker then mounts a tongue depressor 401 on the tool mounting member 115 as exemplarily illustrated in FIG. 4B, places the tongue depressor 401 on the patient's tongue, and depresses the tongue depressor 401 to obtain an unobstructed view of the throat.

When the multi-organ imaging system 100 is controlled using one of the control elements, for example, 110b or 110c, on the control panel 109 positioned on the camera body 101 as exemplarily illustrated in FIG. 1 and FIGS. 5A-5C, the stationary, multi-examination illumination unit 103 is activated and the illuminators 104 of the stationary, multi-examination illumination unit 103 produce illumination and emit light towards the throat and skin examination attachment 106. The illuminators 104, in optical communication with the reflective layer 107 positioned along the inner periphery 106c of the throat and skin examination attachment 106 exemplarily illustrated in FIG. 1, produce shadowless illumination without bright spots during the examination and the imaging of the throat. The emitted light reflects off the reflective layer 107 of the throat and skin examination attachment 106, thereby focusing more light on the patient's throat and assisting in production of shadowless illumination during the examination of the throat. The light guard 119 coaxially attached to the inner periphery 103a of the stationary, multi-examination illumination unit 103 exemplarily illustrated in FIG. 2 and FIG. 4A, prevents reflection of light from the stationary, multi-examination illumination unit 103 and the protective filter 108 into the camera lens 102. The light diffuser 120 coupled to the inner periphery 108a of the protective filter 108 exemplarily illustrated in FIG. 3, FIG. 4A, and FIGS. 6A-6B, scatters the light received from the illuminators 104 of the stationary, multi-examination illumination unit 103 to produce shadowless light for illuminating the target area.

When the health care worker aims the multi-organ imaging system 100 at the throat, the industrial camera unit 118, in operable communication with the camera lens 102, captures an image or a video stream of the throat, which is illuminated by the stationary, multi-examination illumination unit 103. The display unit 125 assists the health care worker in aiming the camera lens 102 and visualizing the throat. When the health care worker touches or clicks on the control element 110a on the control panel 109 or the control element 126a such as the snap button displayed on the GUI 126 of the display unit 125 exemplarily illustrated in FIG. 5B, the industrial camera unit 118 via the camera lens 102 exemplarily illustrated in FIGS. 1-2, captures a snapshot or a video of the target area of the throat. In an embodiment, the multi-organ imaging system 100 communicates the activation of the control element 110a, and in turn, the capture of the snapshot or the video, to the health care worker by providing an audio signal to the health care worker.

The industrial camera unit 118 transmits the captured image or the video to the external computing device 501 via the connector 113a and the media and power cable 114 and further to the display unit 125 from the external computing device 501 via a wireless connection 503 defined by a wireless communication protocol exemplarily illustrated in FIG. 5C. The health care worker may request the patient to make high-pitched or low-pitched sounds to allow the health care worker to view the larynx and watch the vocal cords move on the display unit 125. The display unit 125 displays the captured image or the video without bright spots. After the examination is completed, the health care worker detaches the display holder 122 with the display unit 125 from the spherical mount 112 of the multi-organ imaging system 100. The health care worker may analyze the images or video on the external computing device 501 at a later time. The health care worker may also use the throat and skin examination attachment 106 for examining the skin of the patient. For the skin examination, the health care worker mounts the skin attachment 402 on the tool mounting member 115 of the multi-organ imaging system 100 as exemplarily illustrated in FIG. 4C, places the ring-shaped element 402b on the patient's skin, and proceeds with the skin examination using the multi-organ imaging system 100.

The examples disclosed above indicate use of the multi-organ imaging system 100 in performing ear, nose, and throat (ENT) imaging, skin imaging, retinal imaging, etc., without requiring replacement of the single, integrated, multi-examination illumination unit 103 when changing from one type of examination to another.

The foregoing examples and illustrative implementations of various embodiments have been provided merely for explanation and are in no way to be construed as limiting of the embodiments disclosed herein. Dimensions and measurements disclosed above are exemplary, and are not limiting of the scope of the embodiments herein. While the embodiments have been described with reference to various illustrative implementations, drawings, and techniques, it is understood that the words, which have been used herein, are words of description and illustration, rather than words of limitation. Furthermore, although the embodiments have been described herein with reference to particular means, materials, techniques, and implementations, the embodiments herein are not intended to be limited to the particulars disclosed herein; rather, the embodiments extend to all functionally equivalent structures, methods and uses, such as are within the scope of the appended claims. It will be understood by those skilled in the art, having the benefit of the teachings of this specification, that the embodiments disclosed herein are capable of modifications and other embodiments may be effected and changes may be made thereto, without departing from the scope and spirit of the embodiments disclosed herein.

We claim:

1. A multi-organ imaging system with a single, multi-examination illumination unit, the multi-organ imaging system comprising:
    a camera body comprising a first end, a second end, and a cavity defined between the first end and the second end, wherein a camera unit is housed within the cavity of the camera body, and wherein the camera unit is configured for imaging a plurality of organs;
    a camera lens operably coupled to the camera unit, wherein the camera lens has a fixed focal length and an iris for examination and the imaging of the plurality of organs using the camera unit;
    a stationary, multi-examination illumination unit integrated to the camera body, proximal to the camera lens, wherein the stationary, multi-examination illumination unit comprises a plurality of illuminators arranged in a geometrical configuration thereon; and
    an attachment holder attached to the first end of the camera body, in coaxial communication with the stationary, multi-examination illumination unit positioned in front of the attachment holder, wherein the attachment holder coaxially accommodates an organ examination attachment selected for examining one or more of the plurality of organs, wherein the illuminators of the stationary, multi-examination illumination unit, in optical communication with one or more reflective surfaces in the organ examination attachment, produce shadowless illumination without bright spots during the examination and the imaging of each of the plurality of organs, without requiring replacement of the stationary, multi-examination illumination unit for the examination and the imaging of the each of the organs, wherein the camera unit, in optical communication with the camera lens, captures and displays images of a target area of one of the organs, wherein the camera unit stores a plurality of imaging parameters that are invoked at activation of the multi-organ imaging system, and wherein the imaging parameters comprise a predefined red, green, and blue (RGB) gamma value, front light illumination, front light compensation, daylight color balance, auto white balance, fixed white balance, auto exposure activation, and optional image sharpening.

2. The multi-organ imaging system of claim 1, further comprising a display mounting member operably coupled to and extending outwardly from the second end of the camera body, wherein the display mounting member is detachably attached to a clamping member of a display holder, wherein the display holder is configured to accommodate a display unit, and wherein the display unit receives a media stream of each of the visualized one or more of the plurality of organs captured by the camera unit via the camera lens.

3. The multi-organ imaging system of claim 2, wherein the display mounting member is spherically shaped for allowing movement of the display unit accommodated in the display holder, in multiple dimensions.

4. The multi-organ imaging system of claim 1 configured for performing ear, nose, and throat (ENT) imaging, skin imaging, and retinal imaging, without requiring replacement of the single, integrated, multi-examination illumination unit when one type of examination is changed to another type of examination, wherein the plurality of organs comprises ear, nose, throat, skin, and eyes.

5. The multi-organ imaging system of claim 1, wherein the camera lens is selected to provide a field of view in a body cavity of a patient and a view of an entirety of a mouth of the patient when the camera body is positioned at a predefined distance from a throat of the patient.

6. The multi-organ imaging system of claim 1, wherein the attachment holder is a ring-shaped element for coaxially accommodating the organ examination attachment thereon.

7. The multi-organ imaging system of claim 1, further comprising a reflective layer positioned in the organ examination attachment.

8. The multi-organ imaging system of claim 1, wherein the organ examination attachment is selected from one of a throat and skin examination attachment and an otoscope attachment.

9. The multi-organ imaging system of claim 1, further comprising a protective filter coaxially positioned on a front end of the organ examination attachment over the camera lens and the stationary, multi-examination illumination unit, wherein the protective filter protects the camera lens and the illuminators of the stationary, multi-examination illumination unit, and wherein the illuminators are positioned away from an optical axis passing through the camera body, at a distance from an outer edge of the protective filter.

10. The multi-organ imaging system of claim 9, further comprising a light diffuser coupled to an inner periphery of the protective filter for scattering light received from the illuminators of the stationary, multi-examination illumination unit for producing shadowless light for illuminating the fall target area.

11. The multi-organ imaging system of claim 9, further comprising a light guard positioned proximal to the camera lens and the stationary, multi-examination illumination unit for preventing reflection of light from the stationary, multi-examination illumination unit and the protective filter into the camera lens.

12. The multi-organ imaging system of claim 1, further comprising a tool mounting member attached to the first end of the camera body, wherein the tool mounting member is configured to mount and detachably attach a medical tool that allows an unobstructed view of one of the organs during the examination and the imaging of the one of the organs.

13. The multi-organ imaging system of claim 1, further comprising a control element positioned on one of the camera body, a display unit accommodated in a display holder detachably attached to the camera body, and a remote device operably connected to the multi-organ imaging system via a network, wherein activation of the control element triggers a capture of a snapshot of the fall target area of one of the organs by the camera unit via the camera lens, and wherein the activation of the control element is communicated to an operator of the multi-organ imaging system via an audio signal.

14. The multi-organ imaging system of claim 1, further comprising one or more control elements positioned on an outer surface of the camera body for adjusting illumination settings of the stationary, multi-examination illumination unit.

15. The multi-organ imaging system of claim 1, further comprising a connector positioned on the second end of the camera body for connecting a media and power cable to the camera unit in the camera body and transmit a media stream of each of the one or more of the plurality of organs captured by the camera unit via the camera lens, to an external computing device, and to receive commands from the external computing device.

16. The multi-organ imaging system of claim 1, further comprising gripping elements attached to an outer surface of the camera body for providing a non-slip grip of the camera body to an operator of the multi-organ imaging system.

17. The multi-organ imaging system of claim 1, wherein the illuminators of the stationary, multi-examination illumination unit are selected from surface mount technology light emitting diodes and through-hole light emitting diodes.

* * * * *